(12) United States Patent
Wierckx et al.

(10) Patent No.: US 9,309,546 B2
(45) Date of Patent: Apr. 12, 2016

(54) GENETICALLY MODIFIED CELL AND PROCESS FOR USE OF SAID CELL

(75) Inventors: Nick Johannes Petrus Wierckx, Delft (NL); Tom Daniel Elink Schuurman, Zoetermeer (NL); Sipko Maarten Kuijper, Delfgauw (NL); Harald Johan Ruijssenaars, Driebergen (NL)

(73) Assignee: Purac Biochem B.V., Gorinchem (NL)

( * ) Notice: Subject to any disclaimer, the term of this patent is extended or adjusted under 35 U.S.C. 154(b) by 199 days.

(21) Appl. No.: 14/003,386

(22) PCT Filed: Mar. 7, 2012

(86) PCT No.: PCT/NL2012/050141
§ 371 (c)(1),
(2), (4) Date: Nov. 25, 2013

(87) PCT Pub. No.: WO2012/064195
PCT Pub. Date: May 18, 2012

(65) Prior Publication Data
US 2014/0073019 A1     Mar. 13, 2014

(30) Foreign Application Priority Data
Mar. 8, 2011 (NL) .................................. 2006359

(51) Int. Cl.
*C07K 14/195* (2006.01)
*C12P 17/04* (2006.01)
*C12N 9/02* (2006.01)

(52) U.S. Cl.
CPC ............. *C12P 17/04* (2013.01); *C12N 9/0008* (2013.01)

(58) Field of Classification Search
CPC .............................. C07K 14/195; C12N 9/008
USPC ......... 435/92, 126, 161, 189, 190, 191, 232.2
See application file for complete search history.

(56) References Cited

U.S. PATENT DOCUMENTS

2011/0086395 A1 * 4/2011 Koopman et al. ............... 435/92

FOREIGN PATENT DOCUMENTS

| WO | 2011026906 | 3/2011 |
| WO | WO 2011026906 A2 | 3/2011 |
| WO | WO 2011026913 A1 | 3/2011 |

OTHER PUBLICATIONS

Written Opinion—PCT/NL2012/050141.*
International Search Report for PCT/NL2012/050141 Mailed July 10, 2012.
Database Uniprot [Online], Database Accession No. B1M730, "XP-002660638", (Apr. 2008).
Database Uniprot [Online], Database Accession No. Q4J779, "XP-002660639", (Aug. 2005).
Koopman, et al., "Efficient whole-cell biotransformation of 5-(hydroxymethyl)furfural into FDCA, 2,5-furandicarboxylic acid", Bioresource Technology (Aug. 2010), 101(16):6291-6296.
Koopman, et al., "Identification and characterization of the furfural and 5-(hydroxymethyl)furfural degradation pathways of Cupriavidus basilensis HMF14", Proc Natl Acad Sci USA (Mar. 2010), 107(11):4919-4924.
Koopman, et al., "Identification and characterization of the furfural and 5-(hydroxymethyl)furfural degradation pathways of Cupriavidus basilensis HMF14, supplemental information", Proc Nati Acad Sci USA (Mar. 2010), 107 (11):1-4.
Ribeiro, et al., "Cooperative effect of cobalt acetylacetonate and silica in the catalytic cyclization and oxidation of fructose to 2, 5-furandicarboxylic acid", Catalysis Communications (2003), 4(2):83-86.

* cited by examiner

*Primary Examiner* — Tekchand Saidha
(74) *Attorney, Agent, or Firm* — Bret E. Field; Bozicevic, Field & Francis LLP

(57) ABSTRACT

The present invention relates to the field of biotransformation of furanic compounds. More particular the present invention relates to novel genetically modified cells with improved characteristics for biocatalytic transformation of furanic compounds and a vector suitable for the genetic modification of a host cell. Further aspects of the invention are aimed at processes for biotransformation of 5-(hydroxymethyl)furan-2-carboxylic acid (HMF-acid) and its precursors with the use of the cell according to the invention.

22 Claims, 7 Drawing Sheets

GENETICALLY MODIFIED CELL AND PROCESS FOR USE OF SAID CELL

CROSS REFERENCE TO RELATED APPLICATIONS

This application is a §371 National Stage Application of PCT/NL2012/050141, filed Mar. 7, 2012, which claims priority to Netherlands Application No. 2006359, filed Mar. 8, 2011.

BACKGROUND OF THE INVENTION

1. Field of the Invention

The present invention in general relates to the field of biotransformation of furanic compounds. Such biotransformations find utility in the production of furan-2,5-dicarboxylic acid (FDCA) and processing of lignocellulose containing material e.g. for the production of biofuels and biochemicals. More particular the present invention relates to novel genetically modified cells with improved characteristics for biocatalytic transformation of furanic compounds. A further aspect of the invention relates to a vector suitable for genetic modification of a host cell to improve its characteristics for biotransformation of furanic compounds. Other aspects of the invention relate to processes for biotransformation of 5-(hydroxymethyl)furan-2-carboxylic acid (HMF-acid) and its precursors with the use of the cell according to the invention.

2. Description of Related Art

Biotransformation of furanic compounds is receiving increasing attention. This is both in respect of the bioproduction of furan-2,5-dicarboxylic acid (FDCA), which is a promising value added chemical from biomass (Werpy et al. (2004)), and in respect of their negative role in the fermentative production of biofuels and biochemicals from lignocellulose containing materials (Almeida et al. (2009)).

Recently a furanic compound utilising organism, *Cupriavidus basilensis* HMF14, has been isolated (Koopman et al. (2010a). This organism is capable of metabolizing furfural and 5-(hydroxymethyl)furan-2-carbaldehyde (HMF). The furfural and HMF degradation pathway of *Cupriavidus basilensis* HMF14 has been disclosed by Koopman et al. (2010a) together with the genes involved.

The functional introduction of the hmfH gene from *Cupriavidus basilensis* HMF14 in *Pseudomonas putida* S12 is disclosed by Koopman et al. (2010b). The resulting strain has good FDCA production capabilities using HMF as a substrate. However, the observed accumulation of 5-(hydroxymethyl)furan-2-carboxylic acid (HMF-acid) would require long process times or alternative measures to remove this by-product. Sufficient removal of the HMF-acid by-product is desirable for many of the applications for which the FDCA may be produced and sometimes even is essential.

In search of a solution of the problem of HMF-acid accumulation, the inventors of the present invention have now surprisingly found that expression of certain polypeptides in the *Pseudomonas putida* S12 FDCA production system, effectively reduces HMF-acid accumulation.

SUMMARY

The present findings of the inventors have resulted in the generalized concept that expression in a host of a polypeptide having an amino acid sequence of SEQ ID. NO. 1 or 2 or its analogues/homologues (such as SEQ ID NO: 3 or 4) together with one or more polypeptides capable of conversion of 5-(hydroxymethyl)furan-2-carboxylic acid (HMF-acid), results in effective HMF-acid bioconversion. Improved HMF-acid bioconversion is beneficial for the elimination of HMF-acid and its furanic precursors from feedstocks wherein furanic compounds are considered to be detrimental, such as feedstocks for ethanologenic fermentations for the production of for example biofuels or for fermentations for the biological production of chemicals. In other applications, improved HMF-acid bioconversion will improve bioproduction of a chemical where HMF-acid is a starting material or an intermediate, such as in FDCA bioproduction.

Accordingly a first object of the invention is a genetically modified cell comprising a first polynucleotide sequence coding for a first polypeptide having an amino acid sequence of SEQ ID. NO: 1, 2, 3 or 4 or its analogues/homologues and a second polynucleotide sequence coding for a second polypeptide having HMF-acid converting activity. The HMF-acid converting polypeptide may be the oxidoreductase encoded by the *Cupriavidus basilensis* HMF14 hmfH gene previously described (Koopman et al. 2010a and Koopman et al. 2010b). According to certain embodiments it is preferred that the genetically modified cell comprises a third polynucleotide sequence coding for a third polypeptide having an amino acid sequence of SEQ ID. NO: 19, 20, 21, 22, 23, 24, 25 or its analogues/homologues. Functional expression of the third amino acid sequences results in aldehyde dehydrogenase activity capable of converting furanic aldehydes.

If the second polypeptide is an oxidoreductase, co-expression of the first polypeptide simultaneously with the oxidoreductase may also improve the quality of a whole-cell biocatalyst comprising the oxidoreductase with respect to biocatalytic FDCA production.

The cell according to the invention is genetically modified by functional introduction of at least the first polynucleotide sequence. Preferably the cell is genetically modified by functional introduction of both the first and second polynucleotide sequence. Alternatively the cell is genetically modified by functional introduction of the first and the third polynucleotide sequence. Functional introduction of all three of the first, the second and the third polynucleotide is a further alternative. A further aspect of the invention relates to a vector suitable for genetic modification of a host cell. The vector comprises a first polynucleotide sequence coding for a first polypeptide having an amino acid sequence of SEQ ID. NO. 1, 2, 3, or 4 or its analogues/homologues and a second polynucleotide sequence coding for a second polypeptide having 5-(hydroxymethyl)furan-2-carboxylic acid (HMF-acid) converting activity. Optionally the vector may comprise a third polynucleotide sequence coding for a third polypeptide having an amino acid sequence of SEQ ID. NO: 19, 20, 21, 22, 23, 24, 25 or its analogues/homologues. Such a vector is suitable to obtain a genetically modified cell according to the invention.

Other aspects of the invention relate to a 5-(hydroxymethyl)furan-2-carboxylic acid (HMF-acid) converting process. This process makes use of the cell according to the invention. According to preferred embodiments this process is suitable for the production of FDCA.

A further aspect of the present invention is aimed at the use of a genetically modified cell according to the invention, for the biotransformation of furanic precursors to FDCA.

BRIEF DESCRIPTION OF THE SEQUENCES

Figure 1:
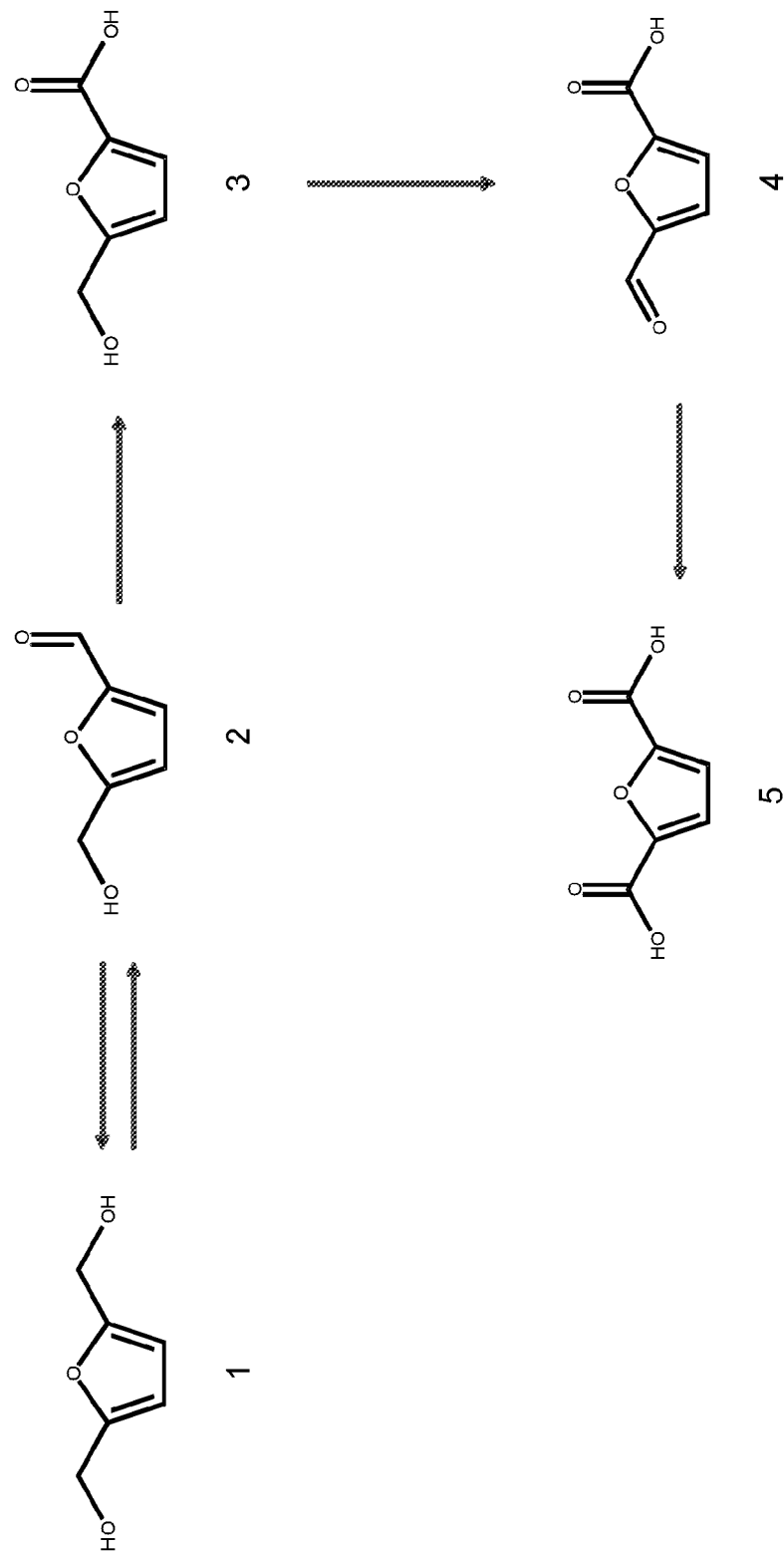
FIG. 1 discloses a schematic representation of oxidative reactions of furanic compounds to 2,5-furan dicarboxylic acid. The following furanic compounds are presented: 1, HMF-alcohol; 2, HMF; 3, HMF-acid; 4, FFA; 5, FDCA.

SEQ ID NO: 1 sets out the amino acid sequence of HmfT1 from *Cupriavidus basilensis* HMF14. The sequence has GenBank accession number ADE20411.1.

SEQ ID NO: 2 sets out the amino acid sequence of HmfT2 from *Cupriavidus basilensis* HMF14. The sequence has GenBank accession number ADE20404.1.

SEQ ID NO: 3 sets out the amino acid sequence of the protein product from the gene with the locus tag mrad2831_4728 from *Methylobacterium radiotolerans* JCM 2831 (=ATCC 27329=DSM 1819). The sequence has GenBank accession number ACB26689.1.

SEQ ID NO: 4 sets out the amino acid sequence of the protein product from the saci_2058 gene from *Sulfolobus acidocaldarius* DSM 639. The sequence has GenBank accession number AAY81352.1.

SEQ ID NO: 5 sets out the amino acid sequence of HmfH from *Cupriavidus basilensis* HMF14. The sequence has GenBank accession number ADE20408.1.

SEQ ID NO: 6 sets out the amino acid sequence of the protein product from the blr0367 gene from *Bradyrhizobium japonicum* USDA 110. The sequence has GenBank accession number BAC45632.1.

SEQ ID NO: 7 sets out the coding sequence of hmfT1 from *Cupriavidus basilensis* HMF14.

SEQ ID NO: 8 sets out the coding sequence of hmfT2 from *Cupriavidus basilensis* HMF14.

SEQ ID NO: 9 sets out the coding sequence of the gene with the locus tag mrad2831_4728 from *Methylobacterium radiotolerans* JCM 2831 (=ATCC 27329=DSM 1819.

SEQ ID NO: 10 sets out the coding sequence of the saci_2058 gene from *Sulfolobus acidocaldarius* DSM 639.

SEQ ID NO: 11 sets out the coding sequence of hmfH from *Cupriavidus basilensis* HMF14.

SEQ ID NO: 12 sets out the coding sequence of the blr0367 gene from *Bradyrhizobium japonicum* USDA 110.

SEQ ID NO: 13-18 set out the sequences of various synthetic primers. Restriction locations (underlined), start and stop (reverse complement) codons (italic) and putative ribosome binding sites (lower case) are indicated. The FN23 primer was designed just upstream of the start codon of hmfH.

SEQ ID NO: 13 sets out the nucleotide sequence of synthetic DNA primer hmfT1 (f)

5'-AC<u>GAATTC</u>AA*aggag*ACAACA*ATG*GAAG-3'

SEQ ID NO: 14 sets out the nucleotide sequence of synthetic DNA primer hmfT1 (r)

5'-AA<u>GCTAGC</u>TGAGCAGTCACCC*TCACTC*-3'

SEQ ID NO: 15 sets out the nucleotide sequence of synthetic DNA primer FN23.

5'-CG<u>GAATTC</u>CACATGACA*aggag*ACCG-3'

SEQ ID NO: 16 sets out the nucleotide sequence of synthetic DNA primer FN24.

5'-CG<u>GAATTC</u>GCTTCGGTCT*TCAACTCGGATG*-3'

SEQ ID NO: 17 sets out the nucleotide sequence of synthetic DNA primer mrad (f).

5'-AC<u>GAATTC</u>*gg*aggAAATCT*ATG*CAGACC-3'

SEQ ID NO: 18 sets out the nucleotide sequence of synthetic DNA primer mrad (r).

5'-AA<u>GCTAGC</u>GCAGAACCGTATCGTCAG-3'

SEQ ID NO: 19 sets out the amino acid sequence of the aldehyde dehydrogenase Adh from *Cupriavidus basilensis* HMF14.

SEQ ID NO: 20 sets out the amino acid sequence having Genbank accession number: YP_003609156.1.

SEQ ID NO: 21 sets out the amino acid sequence having Genbank accession number: ZP_02881557.1.

SEQ ID NO: 22 sets out the amino acid sequence having Genbank accession number: YP_003451184.1.

SEQ ID NO: 23 sets out the amino acid sequence having Genbank accession number: ACA09737.1.

SEQ ID NO: 24 sets out the amino acid sequence having Genbank accession number: YP_530742.1.

SEQ ID NO: 25 sets out the amino acid sequence having Genbank accession number: YP_001541929.1.

SEQ ID NO: 26 sets out the polynucleotide sequence of adh encoding the aldehyde dehydrogenase Adh from *Cupriavidus basilensis* HMF14.

SEQ ID NO: 27 sets out the polynucleotide sequence encoding the amino acid sequence having Genbank accession number: YP_003609156.1.

SEQ ID NO: 28 sets out the polynucleotide sequence encoding the amino acid sequence having Genbank accession number: ZP_02881557.1.

SEQ ID NO: 29 sets out the polynucleotide sequence encoding the amino acid sequence having Genbank accession number: YP_003451184.1.

SEQ ID NO: 30 sets out the polynucleotide sequence encoding the amino acid sequence having Genbank accession number: ACA09737.1.

SEQ ID NO: 31 sets out the polynucleotide sequence encoding the amino acid sequence having Genbank accession number: YP_530742.1.

SEQ ID NO: 32 sets out the polynucleotide sequence encoding the amino acid sequence having Genbank accession number: YP_001541929.1.

SEQ ID NO: 33 sets out the nucleotide sequence of synthetic DNA primer FN13: 5'-AT GCGGCCGCAACAaggagAAGATGGAATGAACG-3' (underlined sequence: NotI restriction site; start codon (ATG) of aldehyde dehydrogenase encoding gene in italics; putative ribosome binding site (RBS) in lower case)

SEQ ID NO: 34 sets out the nucleotide sequence of synthetic DNA primer FN14: 5'-AT GCGGCCGCGCGTCGGGGTCGGTGCTA-3' (underlined sequence: NotI restriction site; stop codon (reverse complement strand) in italics).

DETAILED DESCRIPTION OF A PREFERRED EMBODIMENT

General Definitions

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The term "a number of" should be understood to have the meaning of one or more.

Furanic compounds are herein understood to be any compound having a furan ring. Preferably the furanic compound is a compound that may be oxidized to 2,5-furandicarboxylic acid. Furanic compounds relevant within the context of this invention include [5-(hydroxymethyl)furan-2-yl]methanol ("HMF-alcohol"), 5-(hydroxymethyl)furan-2-carbaldehyde ("HMF"), 5-(hydroxymethyl)furan-2-carboxylic acid ("HMF-acid"), 5-formylfuran-2-carboxylic acid ("FFA"), furan-2,5-dicarbaldehyde (DFF) and furan-2,5-dicarboxylic acid ("FDCA"). The furan ring or any of its substitutable side groups may be substituted, e.g., with OH, C1-C10 alkyl, alkyl, allyl, aryl or RO-ether moiety, including cyclic groups, on any available position in the furan ring. The chemical structures of a number of relevant furanic compounds are presented below.

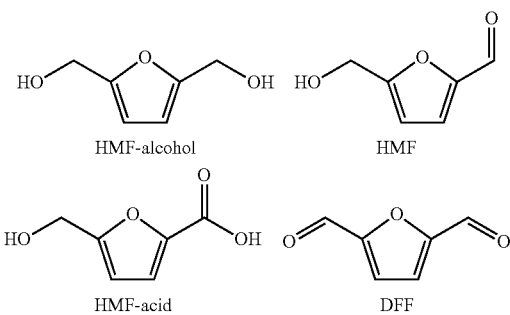

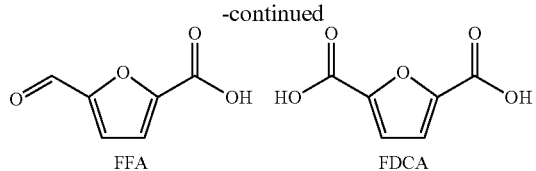

The term "polynucleotide" includes poly deoxyribonucleic acids (DNA) and poly ribonucleic acids (RNA) and the term may refer to either DNA or RNA. The skilled person will be aware of the differences in stability of DNA and RNA molecules. Thus the skilled person will be able to understand from the context of the use of the term "polynucleotide" which of the forms of polynucleotide (DNA and/or RNA) is suitable.

The term sequence "similarity" as used herein refers to the extent to which individual polynucleotide or protein sequences are alike. The extent of similarity between two sequences is based on the extent of identity combined with the extent of conservative changes. The percentage of "sequence similarity" is the percentage of amino acids or nucleotides which is either identical or conservatively changed viz. "sequence similarity"=(% sequence identity)+(% conservative changes).

For the purpose of this invention "conservative changes" and "identity" are considered to be species of the broader term "similarity". Thus whenever, the term sequence "similarity" is used it embraces sequence "identity" and "conservative changes".

The term "sequence identity" is known to the skilled person. In order to determine the degree of sequence identity shared by two amino acid sequences or by two nucleic acid sequences, the sequences are aligned for optimal comparison purposes (e.g., gaps can be introduced in the sequence of a first amino acid or nucleic acid sequence for optimal alignment with a second amino or nucleic acid sequence). Such alignment may be carried out over the full lengths of the sequences being compared. Alternatively, the alignment may be carried out over a shorter comparison length, for example over about 20, about 50, about 100 or more nucleic acids/bases or amino acids.

The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The degree of identity shared between sequences is typically expressed in terms of percentage identity between the two sequences and is a function of the number of identical positions shared by identical residues in the sequences (i.e., % identity=number of identical residues at corresponding positions/total number of positions×100). Preferably, the two sequences being compared are of the same or substantially the same length.

The percentage of "conservative changes" may be determined similar to the percentage of sequence identity. However, in this case changes at a specific location of an amino acid or nucleotide sequence that are likely to preserve the functional properties of the original residue are scored as if no change occurred.

For amino acid sequences the relevant functional properties are the physico-chemical properties of the amino acids. A conservative substitution for an amino acid in a polypeptide of the invention may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —$NH_2$.

For nucleotide sequences the relevant functional properties is mainly the biological information that a certain nucleotide carries within the open reading frame of the sequence in relation to the transcription and/or translation machinery. It is common knowledge that the genetic code has degeneracy (or redundancy) and that multiple codons may carry the same information in respect of the amino acid for which they code. For example in certain species the amino acid leucine is coded by UUA, UUG, CUU, CUC, CUA, CUG codons (or TTA, TTG, CTT, CTC, CTA, CTG for DNA), and the amino acid serine is specified by UCA, UCG, UCC, UCU, AGU, AGC (or TCA, TCG, TCC, TCT, AGT, AGC for DNA). Nucleotide changes that do not alter the translated information are considered conservative changes.

The skilled person will be aware of the fact that several different computer programs, using different mathematical algorithms, are available to determine the identity between two sequences. For instance, use can be made of a computer program employing the Needleman and Wunsch algorithm (Needleman et al. (1970)). According to an embodiment the computer program is the GAP program in the Accelerys GCG software package (Accelerys Inc., San Diego U.S.A). Substitution matrices that may be used are for example a BLOSUM 62 matrix or a PAM250 matrix, with a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

According to an embodiment the percent identity between two nucleotide sequences is determined using the GAP program in the Accelerys GCG software package (Accelerys Inc., San Diego U.S.A) A NWSgapdna CMP matrix and a gap weight of 40, 50, 60, 70, or 80 and a length weight of 1, 2, 3, 4, 5, or 6 is used.

In another embodiment, the percent identity of two amino acid or nucleotide sequences is determined using the algorithm of E. Meyers and W. Miller (Meyers et al. (1989)) which has been incorporated into the ALIGN program (version 2.0) (available at the ALIGN Query using sequence data of the Genestream server IGH Montpellier France http://vega.igh.cnrs.fr/bin/align.guess.cgi) using a PAM120 weight residue table, a gap length penalty of 12 and a gap penalty of 4.

For the present invention it is most preferred to use BLAST (Basic Local Alignment Tool) to determine the percentage identity and/or similarity between nucleotide or amino acid sequences.

Queries using the BLASTn, BLASTp, BLASTx, tBLASTn and tBLASTx programs of Altschul et al. (1990) may be posted via the online versions of BLAST accessible via http://www.ncbi.nlm.nih.gov/. Alternatively a standalone version of BLAST (e.g., version 2.2.24 (released 23 Aug. 2010)) downloadable also via the NCBI internet site may be used. Preferably BLAST queries are performed with the following parameters. To determine the percentage identity and/or similarity between amino acid sequences: algorithm: blastp; word size: 3; scoring matrix: BLOSUM62; gap costs: Existence: 11, Extension: 1; compositional adjustments: conditional compositional score matrix adjustment; filter: off; mask: off. To determine the percentage identity and/or similarity between nucleotide sequences: algorithm: blastn; word size: 11; max matches in query range: 0; match/mismatch scores: 2, −3; gap costs: Existence: 5, Extension: 2; filter: low complexity regions; mask: mask for lookup table only.

The percentage of "conservative changes" may be determined similar to the percentage of sequence identity with the aid of the indicated algorithms and computer programmes. Some computer programmes, e.g., BLASTp, present the number/percentage of positives (=similarity) and the number/percentage of identity. The percentage of conservative changes may be derived therefrom by subtracting the percentage of identity from the percentage of positives/similarity (percentage conservative changes=percentage similarity−percentage identity).

General molecular biological techniques such as hybridization experiments, PCR experiments, restriction enzyme digestions, transformation of hosts etcetera may be performed according to the standard practice known to the skilled person as disclosed in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

First Polynucleotide and Polypeptide

The genetically modified cell according to the invention comprises a first polynucleotide coding for a first polypeptide. The first polypeptide comprises an amino acid sequence having at least 45%, preferably at least 60%, such as at least 70%, more preferably at least 80%, such as 90%, most preferably at least 95% sequence similarity with an amino acid sequence of SEQ ID NO: 1, 2, 3 or 4.

Alternatively the sequence similarity may be expressed as at least, 45%, 50%, 55%, 60%, 65%, 70%, 75%, 80%, 85%, 90%, 91%, 92%, 93%, 94%, 95%, 96%, 97%, 98% or at least 99% similarity. According to an embodiment the indicated percentages similarity may be percentages identity. In a particular embodiment the first polypeptide may comprise the amino acid sequence as set out in any of SEQ ID NO: 1, 2, 3 or 4.

Such a polypeptide is capable of providing an improvement with respect to HMF-acid bioconversion.

Without wishing to be bound by any theory it is believed that such a polypeptide has HMF-acid transport capabilities. By transportation of HMF-acid into the cell by the first polypeptide it becomes better available for intracellular conversion. Thus HMF-acid bioconversion may be improved.

Such an improvement on HMF-acid bioconversion has been shown in the examples for HmfT1 (SEQ ID NO: 1) and the protein product from the gene with the locus tag mrad2831_4728 from Methylobacterium radiotolerans JCM 2831 (=ATCC 27329=DSM 1819) (SEQ ID NO: 3). On the basis of the level of sequence similarity/identity with these sequences it is justified to expect that HmfT2 (SEQ ID NO: 2) and the protein product from the Saci_2058 gene from Sulfolobus acidocaldarius DSM 639 will have similar effects.

HmfT2 (SEQ ID NO: 2) has over 90% similarity with HmfT1 (SEQ ID NO: 1). The level of identity is 87%.

A similar functionality for the protein product of the saci_2058 gene from *Sulfolobus acidocaldarius* DSM 639 (SEQ ID NO: 4) may be expected based on a CLUSTALW2 multiple sequence alignment with transporters from different functional families. The *Sulfolobus* transporter forms a cluster with HmfT1 (SEQ ID NO: 1) and Mrad2831_4728 (SEQ ID NO: 3). Moreover, analysis of the *S. acidocaldarius* genome has shown that the transporter gene saci_2058 is flanked by genes that encode similar functionalities as the hmf gene clusters, respectively, the type of activities that are expected in degradation of HMF(-like) compounds). Examples: Saci_2057, alcohol dehydrogenase; Saci_2059/2060, aromatic ring dioxygenase; Saci_2062, acyl-CoA synthetase (functionally comparable to hmfD); Saci_2063, enoyl-CoA hydratase (functionally comparable with hmfE); Saci_2064, aldehyde oxidase/xanthine dehydrogenase (functionally comparable to hmfABC). On the basis of this analysis it is justified to expect that the protein product of the Saci_2058 gene from *Sulfolobus acidocaldarius* DSM 639 (SEQ ID NO: 4) will have similar effects as HmfT1 (SEQ ID NO: 1) and/or the protein product from the gene with the locus tag mrad2831_4728 from *Methylobacterium radiotolerans* JCM 2831 (=ATCC 27329=DSM 1819) (SEQ ID NO: 3).

The first polypeptide may be encoded by a first polynucleotide sequence having at least 45%, preferably at least 60%, such as at least 70%, more preferably at least 80%, such as 90%, most preferably at least 95% sequence similarity with a polynucleotide sequence set out in SEQ ID NO: 7, 8, 9 or 10. Suitable alternative levels of similarity of the first polynucleotide with a sequence set out in SEQ ID NO: 7, 8, 9 or 10 may be at least 66%, 70%, 75%, 80%, 85%, 90%, 91%, 92%, 93%, 94%, 95%, 96%, 97%, 98% or at least 99% similarity. According to an embodiment the indicated percentages similarity may be percentages identity. In a particular embodiment the first polypeptide may be coded by a polynucleotide sequence as set out in SEQ ID NO 7, 8, 9 or 10.

The first polypeptide or the polynucleotide coding for the first polypeptide may be isolated from an organism, preferably a microorganism that expresses the first polypeptide under certain growth conditions. The microorganism may be capable of using HMF-acid or related furanic substances, such as HMF or HMF-alcohol, as carbon source, but this is not necessary.

In a typical approach, gene libraries can be screened to isolate alternative polynucleotides which are suitable. The libraries may be constructed from microorganisms from the superkingdom of Bacteria. These microorganisms may belong to the phylum of Proteobacteria, more specifically to the class of Alphaproteobacteria or Betaproteobacteria. The Alphaproteobacteria may belong to the order of Rhizobiales, to the families of Bradyrhizobiaceae or Methylobacteriaceae. The Bradyrhizobiaceae may belong to the genus *Bradyrhizobium*, e.g., *Bradyrhizobium japonicum*, or to the genus of *Afipia*. The Methylobacteriaceae may belong to the genus of *Methylobacterium*, e.g., *Methylobacterium nodulans* or *Methylobacterium radiotolerans*. The Betaproteobacteria may belong to the order of Burkholderiales, more specifically the family of Burkholderiaceae. They may belong to the genus *Cupriavidus*, e.g., *Cupriavidus basilensis*; or to the genus *Ralstonia*, e.g., *Ralstonia eutropha*; or to the genus *Burkholderia*, e.g., *Burkholderia phymatum, Burkholderia phytofirmans, Burkholderia xenovorans*, or *Burkholderia graminis*. The bacteria may also belong to the phylum of Firmicutes, more specifically the class of Bacilli, more specifically the order of Bacillales. The Bacillales may belong to the family of Bacillaceae, more specifically to the genus *Geobacillus*, e.g., *Geobacillus kaustophilus*. Alternatively, the microorganisms may belong to the superkingdom of Archaea, more specifically the phylum of Euryarchaeota, or the phylum of Crenarchaeota. The Euryarchaeota may belong to an unclassified genus, e.g., Cand. *Parvarchaeum acidiphilum*, or to the class of Thermoplasmata, more specifically the order of Thermoplasmatales. The Thermoplasmatales may belong to the family of Thermoplasmataceae, more specifically the genus *Thermoplasma*, e.g., *Thermoplasma acidophilum* or *Thermoplasma volcanium*. The Crenarchaeota may belong to the class of Thermoprotei, more specifically the order of Sulfolobales. The Sulfolobales may belong to the family of Sulfolobaceae, more specifically the genus *Sulfolobus*, e.g., *Sulfolobus acidocaldarius, Sulfolobus islandicus, Sulfolobus solfataricus*, or *Sulfolobus tokodaii*; or to the genus of *Metallosphaera*, e.g., *Metallosphaera sedula*. The Thermoprotei may also belong to the order of Thermoproteales, family of Thermoproteaceae. The Thermoproteaceae may belong to the genus *Vulcanisaeta*, e.g., *Vulcanisaeta distributa*; or to the genus *Caldivirga*, e.g., *Caldivirga maquilingensis*.

Preferably the first polypeptide and/or the first polynucleotide coding for the first polypeptide is isolated from *Cupriavidus basilensis* HMF14 (Wierckx et al. 2010). According to an alternative embodiment the first polypeptide and/or the first polynucleotide coding for the first polypeptide may be isolated from *Methylobacterium radiotolerans*.

Based on the amino acid sequences provided in SEQ. ID. NO: 1, 2, 3 or 4 and/or the nucleotide sequences provided in SEQ. ID. NO: 7, 8, 9 or 10, the skilled person will be able to construct suitable probes and/or primers to isolate a nucleotide sequence coding for the first polypeptide.

Alternatively, based on the amino acid sequences provided in SEQ. ID. NO: 1, 2, 3 or 4 and/or the nucleotide sequences provided in SEQ. ID. NO: 7, 8, 9 or 10, the skilled person may obtain synthesized sequences coding for the first polypeptide from commercial sources, as gene synthesis is becoming increasingly available. Synthetic sequences may be purchased for example from Geneart A.G. (Regensburg, Germany) or from Genscript USA Inc. (Piscataway, N.J., USA) to name but a few.

The cell according to the invention is genetically modified by functional introduction of the first polynucleotide. With functional introduction of a polynucleotide is meant, an introduction of said polynucleotide in a cell, such that said cell acquires the possibility to express a functional polypeptide product of the polynucleotide. Methods and techniques for functional introduction of polynucleotides in host cells are within the general knowledge of the skilled person.

HMF-Acid Converting Polypeptide

The genetically modified cell according to the invention comprises a second polynucleotide coding for a second polypeptide. The second polypeptide has HMF-acid converting activity and may be selected from any polypeptide capable of converting HMF-acid to a product. The inventors have observed that bioconversion of HMF-acid by the HMF-acid converting second polypeptide, is effectively improved by expression of the first polypeptide in a cell.

The second polynucleotide coding for the second polypeptide may be a natural component of the cell according to the invention viz. the cell need not be genetically modified in respect of the second polynucleotide. However, according to certain embodiments of the invention the cell according to the invention is genetically modified in respect of the second polynucleotide, by functional introduction of the second polynucleotide. The term "functional introduction" has already been explained above in connection to the first polypeptide and first polynucleotide.

According to a preferred embodiment of the invention, the second polypeptide is an HMF-acid converting oxidoreductase. This HMF-acid converting oxidoreductase may comprise an amino acid sequence set out in SEQ ID NO: 5 or 6 or a variant polypeptide thereof having at least 45%, preferably at least 60%, such as at least 70%, more preferably at least 80%, such as 90%, most preferably at least 95% sequence similarity with the amino acid sequence set out in SEQ ID NO 5 or 6.

Alternatively the sequence similarity may be at least, 45%, 50%, 55%, 60%, 65%, 70%, 75%, 80%, 85%, 90%, 91%, 92%, 93%, 94%, 95%, 96%, 97%, 98% or at least 99% similarity. According to an embodiment the indicated percentages similarity may be percentages identity. In a particular embodiment the second polypeptide may comprise the amino acid sequence as set out in any of SEQ ID NO: 5 or 6.

The HMF-acid converting oxidoreductase of SEQ ID NO: 5 was previously disclosed by Koopman et al. (2010a) and Koopman et al. (2010b) and designated HmfH. The HMF-acid converting oxidoreductase of SEQ ID NO: 6 may be isolated from *Bradyrhizobium japonicum* USDA 110 and corresponds to the translated protein product of the blr0367 gene. *B. japonicum* USDA 110 contains homologues for all HMF/furfural utilization genes from *C. basilensis* HMF14 in its genome (Koopman et al. 2010a). The translated product of the blr0367 gene is the protein of *B. japonicum* USDA 110 that showed highest homology to HmfH from *C. basilensis* HMF14. In view of the fact that *B. japonicum* USDA 110 was shown to utilize HMF as the sole carbon source (Koopman et al. 2010a) it must harbour a functional HmfH homologue. It is therefore justified to expect that HmfH similar activity arises from blr0367.

Although the invention is exemplified with reference to a number of HMF-acid converting oxidoreductases it should be noted that within the invention it is expressly permitted that the second polypeptide is a different HMF-acid converting oxidoreductase or yet a different HMF-acid converting polypeptide not having oxidoreductase activity.

The second polypeptide may be encoded by a second polynucleotide sequence having at least 45%, preferably at least 60%, such as at least 70%, more preferably at least 80%, such as 90%, most preferably at least 95% sequence similarity with a polynucleotide sequence set out in SEQ ID NO: 11 or 12. Suitable alternative levels of similarity of the first polynucleotide with a sequence set out in SEQ ID NO: 11 or 12 may be at least 66%, 70%, 75%, 80%, 85%, 90%, 91%, 92%, 93%, 94%, 95%, 96%, 97%, 98% or at least 99% similarity. In an embodiment the indicated percentages similarity may be percentages identity. In a particular embodiment the second polypeptide may be coded by a polynucleotide sequence as set out in SEQ ID NO 11 or 12.

Isolation of a suitable polynucleotide coding for the second polypeptide having oxidoreductase activity from *Cupriavidus basilensis* has been disclosed in Koopman et al. (2010a). This gene is designated hmfH.

In an approach for isolation of the second polynucleotide, gene libraries can be screened to isolate polynucleotides which are suitable. The libraries may be constructed from microorganisms from the superkingdom of Bacteria. These microorganisms may belong to the phylum of Proteobacteria, more specifically to the class of Alphaproteobacteria, Betaproteobacteria, or Gammaproteobacteria. The Alphaproteobacteria may belong to the order of Rhizobiales, or the order of Sphingomonadales. The Rhizobiales may belong to the family of Methylobacteriaceae, e.g., an organism from the genus *Methylobacterium* such as *M. nodulans* or *M. radiotolerans*, or an organism from the family of Rhizobiaceae. The Rhizobiaceae may belong to the *Rhizobium/Agrobacterium* group, more specifically to the genus *Rhizobium*, such as *R. leguminosarum* or *R. leguminosarum* bv. *trifolii*. They may also belong to the genus *Agrobacterium*, such as *A. radiobacter*. The Rhizobiaceae may also belong to the family of Bradyrhizobiaceae, more specifically the genus of *Bradyrhizobium*, such as *B. japonicum*. Sphingomonedales may belong to the family of Sphingomonadaceae, more specifically to the genus of *Sphingomonas*, such as *S. wittichii* or *S. chlorophenolicum*. The Betaproteobacteria may belong to the order of the Methylophilales, or the order of Burkholderiales. The Methylophilales may belong to the family of Methylophilaceae, e.g., an organism from the genus *Methylovorus*. The Burkholderiales may belong to the family of Burkholderiaceae, e.g., an organism from the genus *Cupriavidus*, such as *Cupriavidus basilensis*. They may also belong to the genus *Burkholderia*, such as *Burkholderia phytofirmans*. *B. phymatum*, *B. graminis*, *B. xenovorans*, or *B. cenocepacia*, or to the family of Oxalobacteraceae, genus of *Janthinobacterium*. The Gammaproteobacteria may belong to the order of Enterobacteriales, family of Enterobacteriaceae, genus of *Yersinia* such as *Yersinia ruckeri*. The microorganisms may furthermore be bacteria of the phylum of Actinobacteria, class of Actinobacteria, subclass of Actinobacteridae, order of Actinomycetales. The Actinomycetales may belong to the suborder of Streptomycineae, Pseudonocardineae, or Micromonosporineae. The Streptomycineae may belong to the family of Streptomycetaceae, more specifically the genus *Streptomyces*, such as *S. violaceusniger, S. hygroscopicus*, or *S. clavuligerus*. The Pseudonocardineae may belong to the family of Pseudonocardiaceae, more specifically the genus of *Saccharopolyspora* such as *S. erythraea*; or to the family of Actinosynnemataceae, more specifically to the genus of *Saccharothrix* such as *S. mutabilis*, or *S. mutabilis* subsp. *capreolus*, or to the genus *Actinosynnema*, such as *A. mirum*. The Micromonosporineae may belong to the family of Micromonosporaceae, more specifically the genus of *Micromonospora*.

Based on the amino acid sequences provided in SEQ. ID. NO: 5 or 6 and/or the nucleotide sequences provided in SEQ. ID. NO: 11 or 12, the skilled person will be able to construct suitable probes and/or primers to isolate a nucleotide sequence coding for the second polypeptide.

Alternatively, based on the amino acid sequences provided in SEQ. ID. NO: 5 or 6 and the nucleotide sequences provided in SEQ. ID. NO: 11 or 12, the skilled person may obtain synthesized sequences coding for the second polypeptide from commercial sources as already indicated in the section discussing the first polypeptide.

Third Polynucleotide and Polypeptide

According to an alternative embodiment the genetically modified cell according to the invention comprises a third polynucleotide coding for a third polypeptide. The third polypeptide comprises an amino acid sequence having at least 45%, preferably at least 60%, such as at least 70%, more preferably at least 80%, such as 90%, most preferably at least 95% sequence similarity with an amino acid sequence of SEQ ID NO: 19, 20, 21, 22, 23, 24 or 25.

Alternatively the sequence similarity may be expressed as at least, 45%, 50%, 55%, 60%, 65%, 70%, 75%, 80%, 85%, 90%, 91%, 92%, 93%, 94%, 95%, 96%, 97%, 98% or at least 99% similarity. According to an embodiment the indicated percentages similarity may be percentages identity. In a particular embodiment the first polypeptide may comprise the amino acid sequence as set out in any of SEQ ID NO: 19, 20, 21, 22, 23, 24 or 25. The amino acid sequence of SEQ ID NO: 19 is a preferred selection of the third polypeptide. This amino acid sequence was recently published in WO2011/026906 (SEQ ID NO:15).

Functional expression of such a third polypeptide results in aldehyde dehydrogenase activity (Adh) capable of converting furanic aldehydes and provides a further improvement with respect to HMF-acid bioconversion and/or FDCA production.

The effects associated with the expression of the third polypeptide have been shown in the examples for the amino acid sequence of SEQ ID NO: 19. On the basis of the level of sequence similarity/identity it is justified to expect that the polypeptides of SEQ ID 20-25 and their analogues/homologues will have similar effects.

The third polypeptide may be encoded by a third polynucleotide sequence having at least 45%, preferably at least 60%, such as at least 70%, more preferably at least 80%, such as 90%, most preferably at least 95% sequence similarity with a polynucleotide sequence set out in SEQ ID NO: 26, 27, 28, 29, 30, 31 or 32. Preferably the third polypeptide is encoded by a polynucleotide sequence set out in SEQ ID NO 26 or a homologue having the indicated sequence similarity with the polynucleotide sequence set out in SEQ ID NO: 26. The polynucleotide sequence of SEQ ID NO: 26 was recently published in WO2011/026906 (SEQ ID NO:16). Suitable alternative levels of similarity of the third polynucleotide with a sequence set out in SEQ ID NO: 26, 27, 28, 29, 30, 31 or 32 may be at least 66%, 70%, 75%, 80%, 85%, 90%, 91%, 92%, 93%, 94%, 95%, 96%, 97%, 98% or at least 99% similarity. According to an embodiment the indicated percentages similarity may be percentages identity. In a particular embodiment the third polypeptide may be coded by a polynucleotide sequence as set out in SEQ ID NO 26, 27, 28, 29, 30, 31 or 32.

Isolation and further manipulation of the third polypeptide and the corresponding third polynucleotide may be performed in general as is discussed above and hereafter for the first polypeptide and the corresponding first polypeptide.

Vectors

Another aspect of the invention pertains to vectors, including cloning and expression vectors, comprising the first and second polynucleotide or a functional equivalent thereof and methods of growing, transforming or transfecting such vectors in a suitable host cell, for example under conditions in which expression of a polypeptide of the invention occurs. As used herein, the term "vector" refers to a nucleic acid molecule capable of transporting another nucleic acid to which it has been linked.

The first and second polynucleotide and optionally the third polynucleotide, can be incorporated into a recombinant replicable vector, for example a cloning or expression vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below.

The vector into which the expression cassette or polynucleotide of the invention is inserted may be any vector which may conveniently be subjected to recombinant DNA procedures, and the choice of the vector will often depend on the host cell into which it is to be introduced.

A vector according to the invention may be an autonomously replicating vector, i.e. a vector which exists as an extra-chromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated.

One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as cosmid, viral vectors (e.g., replication defective retroviruses, adenoviruses and adeno-associated viruses), phage vectors and transposons and plasposons, which serve equivalent functions.

The skilled person will be able to construct the vectors according to the invention based on the amino acid and polynucleotide sequences provided, his knowledge of the art and commercially available means.

According to a preferred embodiment the first and second polynucleotide sequence are located on a single vector. This vector optionally further comprising the third polynucleotide sequence. As the skilled person will understand, the use of a vector comprising the first and second polynucleotide sequence (and optionally further comprising the third polynucleotide sequence) greatly simplifies construction of genetically modified cells functionally expressing the first and second polypeptide (optionally together with the third polypeptide). However as the skilled person will also understand, genetically modified cells functionally expressing the first and second polypeptide may be obtained via various other transformation schemes involving alternative vectors. In this respect it should be noted that according to certain embodiments, functional introduction of the second polynucleotide sequence is not a requirement. Also according to certain further alternative embodiments, functional introduction of the third polynucleotide sequence is not a requirement.

Host Cell

The genetically modified cell according to the invention may be constructed from any suitable host cell. The host cell may be an unmodified cell or may already be genetically modified. The cell may be a prokaryote cell, a eukaryote cell, a plant cell or an animal cell. In such a cell one or more genes may be deleted, knocked-out or disrupted in full or in part, wherein optionally one or more genes encode for protease.

According to an embodiment, the host cell according to the invention is a eukaryotic host cell. Preferably, the eukaryotic cell is a mammalian, insect, plant, fungal, or algal cell. Preferred mammalian cells include, e.g., Chinese hamster ovary (CHO) cells, COS cells, 293 cells, PerC6 cells, and hybridomas. Preferred insect cells include e.g. Sf9 and Sf21 cells and derivatives thereof. More preferably, the eukaryotic cell is a fungal cell, i.e., a yeast cell, such as *Candida, Hansenula,*

*Kluyveromyces, Pichia, Saccharomyces, Schizosaccharomyces*, or *Yarrowia* strain. More preferably, the eukaryotic cell is *Kluyveromyces lactis, Saccharomyces cerevisiae, Hansenula polymorpha, Yarrowia lipolytica, Pichia stipitis* and *Pichia pastoris*, or a filamentous fungal cell. In certain embodiments, the eukaryotic cell is a filamentous fungal cell.

"Filamentous fungi" include all filamentous forms of the subdivision *Eumycota* and *Oomycota* (as defined by Hawksworth et al., (1995)). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Phanerochaete, Pleurotus, Schizophyllum, Talaromyces, Thermoascus, Thielavia, Tolypocladium*, and *Trichoderma*.

Preferred filamentous fungal cells belong to a species of an *Aspergillus, Chrysosporium, Penicillium, Talaromyces* or *Trichoderma* genus, and most preferably a species selected from *Aspergillus niger, Aspergillus awamori, Aspergillus foetidus, Aspergillus sojae, Aspergillus fumigatus, Talaromyces emersonii, Aspergillus oryzae, Chrysosporium lucknowense, Trichoderma reesei* or *Penicillium chrysogenum*.

According to another embodiment, the host cell according to the invention is a prokaryotic cell. Preferably, the prokaryotic host cell is bacterial cell. The term "bacterial cell" includes both Gram-negative and Gram-positive microorganisms. Suitable bacteria may be selected from, e.g., the genera *Escherichia, Anabaena, Caulobacter, Gluconobacter, Rhodobacter, Pseudomonas, Paracoccus, Bacillus, Brevibacterium, Corynebacterium, Rhizobium (Sinorhizobium), Bradyrhizobium, Flavobacterium, Klebsiella, Enterobacter, Lactobacillus, Lactococcus, Methylobacterium, Staphylococcus, Streptomyces, Zymomonas, Acetobacter, Streptococcus, Bacteroides, Selenomonas, Megasphaera, Burkholderia, Cupriavidus, Ralstonia, Methylobacterium, Methylovorus, Rhodopseudomonas, Acidiphilium, Dinoroseobacter, Agrobacterium, Sulfolobus* or *Sphingomonas*. Preferably, the bacterial cell is selected from the group consisting of *Bacillus subtilis, Bacillus amyloliquefaciens, Bacillus licheniformis, Bacillus puntis, Bacillus megaterium, Bacillus halodurans, Bacillus pumilus, Gluconobacter oxydans, Caulobacter crescentus, Methylobacterium extorquens, Methylobacterium radiotolerans, Methylobacterium nodulans, Rhodobacter sphaeroides, Pseudomonas zeaxanthinifaciens, Pseudomonas putida, Pseudomonas putida* S12, *Paracoccus denitrificans, Escherichia coli, Corynebacterium glutamicum, Staphylococcus carnosus, Streptomyces lividans, Sinorhizobium meliloti, Bradyrhizobium japonicum, Rhizobium radiobacter, Rhizobium leguminosarum, Rhizobium leguminosarum* bv. *trifolii, Agrobacterium radiobacter, Cupriavidus basilensis, Cupriavidus necator (Ralstonia eutropha), Ralstonia pickettii, Burkholderia phytofirmans, Burkholderia phymatum, Burkholderia xenovorans, Burkholderia graminis, Rhodopseudomonas palustris, Acidiphilium cryptum, Dinoroseobacter shibae, Sulfolobus acidocaldarius, Sulfolobus islandicus, Sulfolobus solfataricus, Sulfolobus tokodaii*.

A highly preferred host cell is *Pseudomonas putida* S12. In this strain functional expression of the hmfH gene from *Cupriavidus basilensis* HMF14 has proven effective for introducing HMF oxidative capacity, resulting in FDCA production from this substrate.

For specific uses of the cell according to the invention, the selection of the host cell may be made according to such use. Particularly preferred are those hosts that are suitable for conversion of lignocellulosic feed stocks and those which are resistant to the conditions preferred for the production of furanic compounds, such as FDCA. The skilled person will have to his availability suitable means and methods to functionally introduce the first and optionally the second poly nucleotide into any of the mentioned host cells.

HMF-Acid Biotransformation

The genetically engineered cell according to the invention has an improved HMF-acid biotransformation. Improved HMF-acid bioconversion is beneficial for the elimination of HMF-acid and its furanic precursors from feedstocks wherein furanic compounds are considered to be detrimental, such as feedstocks for ethanologenic fermentations for the production of biofuels and biochemicals. In other applications improved HMF-acid bioconversion will improve bioproduction of chemical where HMF-acid is a starting material or an intermediate, such as in FDCA bioproduction.

If the HMF acid-converting enzyme is a HMF-acid converting oxidoreductase, the cell according to the invention will be capable of performing a biological oxidation reaction. The oxidation reaction is herein one or more reactions of an oxidant with HMF-acid in the presence of the oxidoreductase.

A preferred oxidation reaction is the production of FDCA, wherein HMF-acid is converted to FDCA, by reaction with an oxidant in the presence of a HMF-acid converting oxidoreductase. Bioconversions of furanic compounds to FDCA, wherein HMF-acid is an intermediate, have been disclosed in the prior art, for example using HMF as a starting material (see Koopman et al. 2010a and Koopman et al. 2010b). Such bioconversions will be improved if they are performed by a cell according to the invention.

HMF-acid may be generated in situ from one or more furanic precursors by the cell of the invention or any other cell present. With in situ generation is meant that the HMF-acid is not added from outside the system. Instead HMF-acid is generated within the system via one or more bioconversions that convert furanic precursors to HMF-acid.

The furanic precursor of HMF-acid may be chosen from the group consisting of 5-(hydroxymethyl)furan-2-carbaldehyde (HMF), furan-2,5-dicarbaldehyde (DFF) and [5-(hydroxymethyl)furan-2-yl]methanol (HMF alcohol) and preferably the furanic precursor is HMF.

HMF may be obtained from one or more hexose sugars by acid-catalyzed dehydration, as is known in the art. The hexose sugars may be obtained from biomass, preferably lignocellulosic biomass.

The oxidation reaction may comprise a number of consecutive oxidation reaction steps resulting in a product e.g. the oxidation of HMF-acid to FFA and further the oxidation of FFA to FDCA. Examples of oxidation reactions are given in FIG. 1.

The oxidation reactions are preferably conducted at relatively mild temperature, i.e. 10-80° C., more preferably 20-45° C., most preferably around from 25-40° C. It is preferred to conduct the reaction at a pH where FDCA is either in a neutral form or in a fully dissociated form, such that salt formation may be controlled. In view of the presence of two acid moieties in FDCA there are two separate preferred pH ranges. The pH during the reaction may be from pH 1 to 6, preferably from pH 1 to 4, most preferably from pH 1 to 3. Alternatively the pH during the reaction may be from pH 5 to 9, preferably from pH 5 to 8, most preferably from pH 5 to 7. The skilled person will understand that the requirements of the host cell will also influence the selection of a suitable pH value for the process. Selection of pH values that are suitable for the various host cells that are suitable within the present invention is within the ambit of the skilled person and may be derived from standard text books. For *Pseudomonas putida*, including *Pseudomonas putida* S12, the preferred pH range is from pH 5 to 7.

The reaction time may be 6-150 h, with the addition of oxygen from an oxygen source, such as molecular oxygen, or water, or a different source of oxygen depending on the requirements of the furanic oxidizing enzyme. Air may be used conveniently as a source of molecular oxygen.

The reactor may be any suitable (aerated) bioreactor. It may be operated in batch, continuously or fed-batch operation.

After biotransformation, the cells may be separated from the broth by established methods and re-used. Oxidation products such as FDCA, HMF-acid, etc. may be recovered from the reaction mixture by (acid) precipitation and subsequent cooling crystallisation, and separation of the crystallized oxidation product, e.g., crystallized FDCA. However, other recovery methods are suitable, such as but not limited to acid precipitation and solvent extraction, as known in the art.

For many applications, such as removal of HMF-acid from lignocellulosic feedstocks, the exact way of HMF-conversion is irrelevant. What is important is that the HMF-acid is converted effectively in order to remove it as such, or to prevent its accumulation if it is formed from furanic precursors. For such applications the HMF-acid converting polypeptide may be any polypeptide having HMF-converting activity presently known or yet to be discovered.

A further aspect of the present invention is aimed at the use of a genetically modified cell according to the invention, for the biotransformation of furanic precursors to FDCA. The furanic precursors may in particular be selected from 5-(hydroxymethyl)furan-2-carbaldehyde (HMF), [5-(hydroxymethyl)furan-2-yl]methanol (HMF alcohol), furan-2,5-dicarbaldehyde (DFF), 5-(hydroxymethyl)furan-2-carboxylic acid (HMF-acid) or 5-formylfuran-2-carboxylic acid (FFA). Preferably HMF is a selected furanic precursor. HMF-acid may be an intermediate in the bioconversion of HMF to FDCA.

The invention will be further illustrated with reference to the following examples.

EXAMPLES

General Methodology

Strains and Plasmids

*Pseudomonas putida* S12 (ATCC 700801) was used as the host for expression of genes from *Cupriavidus basilensis* HMF14 (Wierckx et al., 2010; Koopman et al. 2010a) and *Methylobacterium radiotolerans* JCM 2831 (=ATCC 27329=DSM 1819; genome sequence available at http://genome.jgi-psf.org/metra/metra.home.html). *Escherichia coli* strains DH5α or TOP10 (Invitrogen) were used for general cloning purposes.

For episomal expression of *C. basilensis* or *M. radiotolerans* genes either the pUCP22-derived pJT'mcs (Koopman et al., 2010a) or pJNNmcs(t) (Wierckx et al., 2008), or the pBBR1MCS-derived pBT'mcs (Koopman et al., 2010a) was used. In pJT'mcs and pBT'mcs the expression of the target gene is driven from the constitutive tac promoter. In pJNNmcs(t) the expression is driven from the salicylate inducible NagR/P$_{nagAa}$ expression cassette.

Media & Culture Conditions

Mineral salts medium (MM) was used as a defined medium. MM contained the following (per liter of demineralized water): 3.88 g of $K_2HPO_4$, 1.63 g of $NaH_2PO_4$, 2.0 g of $(NH_4)_2SO_4$, 0.1 g of $MgCl_2.6H_2O$, 10 mg of EDTA, 2 mg of $ZnSO_4.7H_2O$, 1 mg of $CaCl_2.2H_2O$, 5 mg of $FeSO_4.7H_2O$, 0.2 mg of $Na_2MoO_4.2H_2O$, 0.2 mg of $CuSO_4.5H_2O$, 0.4 mg of $CoCl_2.6H_2O$, and 1 mg of $MnCl_2.2H_2O$, supplemented with a carbon source as specified. Luria broth (L-broth: 10 g/l Bacto trypton (Difco), 5 g/l yeast extract (Difco), 5 g/l NaCl) was used as a complete medium for propagation of *P. putida* S12 and derivative strains, *C. basilensis*, *M. radiotolerans* and *E. coli* DH5α and derivatives. For plate culturing, L-broth was solidified with 1.5% (w/v) of agar (Difco). Ampicillin (Amp) was added to the media to 100 μg/ml for selection of *E. coli* transformants carrying pJT'mcs or pJNNmcs(t)-derived plasmids. Gentamicin (Gm) was added to 30 μg/ml in Luria broth and 10 μg/ml in mineral salts medium for selection of *P. putida* S12 transformants carrying pJT'mcs or pJNNmcs(t)-derived plasmids. For selection of either *E. coli* or *P. putida* S12 transformants carrying pBT'mcs-derived plasmids, 50 μg/ml of kanamycin (Km) was added to the media. Antibiotics were purchased from Sigma-Aldrich. *P. putida*, *C. basilensis* and *M. radiotolerans* were cultured at 30° C.; *E. coli* was cultured at 37° C.

Fed batch experiments with *P. putida* S12-derived strains were performed in 2-L vessels controlled either by a Labfors 4 Bioreactor system (Infors Benelux BV) or a BioFlo110 controller (New Brunswick Scientific). Pressurized air or pure oxygen was supplied either in the head space or sparged through the broth. The temperature was controlled at 30° C. and the pH was maintained at 7.0 by automatic addition of either $NH_4OH$, NaOH or KOH. The batch phase was performed in 2×MM medium, supplemented with strain specific antibiotics and 40 g/l glycerol. For high-cell density cultures, the batch-phase medium was furthermore supplemented with 10 g/l of Yeast Extract (YE). After depletion of the initial glycerol, the feed (4 or 8 M of glycerol in 100 mM $MgCl_2$, supplemented with 1 mM of Na-salicylate when required) was started and controlled to allow for growth while maintaining glycerol as the limiting substrate in the culture. The HMF feed (4M in demineralized water) was fed via a separate feed pump; the feed rate was adjusted depending on the strain employed and the condition studied. The dissolved oxygen tension (DO) was continuously monitored and the stirring speed was adjusted to maintain sufficient aeration.

Assays & Analytical Methods

Cell dry weight (CDW) measurement: CDW content of bacterial cultures was determined by measuring optical density at 600 nm ($OD_{600}$) using a Biowave Cell Density Meter (WPA Ltd) or a μQuant MQX200 universal microplate spectrophotometer (Biotek), using flat-bottom 96-well microplates (Greiner). An $OD_{600}$ of 1.0 corresponds to 0.56 g CDW/L (Biowave) or 1.4 g CDW/L (μQuant) for *P. putida*.

HPLC Analyses:

Furan compounds (FDCA, HMF, HMF-alcohol, HMF-acid and FFA) were analyzed by RP-HPLC as described by Koopman et al. (2010a). Sugars, alcohols and organic acids were also analyzed by HPLC (Agilent 1100 system) using a refractive index (RI) detector. The column used was a Bio-Rad Aminex HPX-87H (300×7.8 mm, hydrogen form, 9 μm particle size, 8% cross linkage, pH range 1-3) with 5 mM $H_2SO_4$ as the eluent at a flow rate of 0.6 ml/min Chemicals HMF was purchased either at Sigma, Eurolabs Ltd (Poynton, UK) or Yore Chemipharm Co. Ltd. (Ningbo, China). Analytical standards of FDCA and 5-hydroxymethyl-furoic acid (HMF acid) were purchased from Immunosource B.V. (Halle-Zoersel, Belgium), respectively, Matrix Scientific (Columbia S.C., USA). All other chemicals were purchased from Sigma-Aldrich Chemie B.V. (Zwijndrecht, The Netherlands).

Molecular and Genetic Techniques:

Genomic DNA was isolated from *C. basilensis* HMF14 and *M. radiotolerans* JCM 2831 using the DNeasy tissue kit (QIAGEN). Plasmid DNA was isolated with the QIAprep spin miniprep kit (QIAGEN). Agarose-trapped DNA fragments were isolated with the QIAEXII gel extraction kit (QIAGEN).

PCR reactions were performed with Accuprime Pfx polymerase (Invitrogen) according to the manufacturer's instructions. Oligonucleotide primers (specified in the examples) were synthesized by MWG Biotech AG (Germany). Plasmid DNA was introduced into electrocompetent cells using a Gene Pulser electroporation device (BioRad). Other standard molecular biology techniques were performed according to Sambrook and Russell (2001).

Example I

Co-Expression of HmfH and HmfT1 Improves FDCA Production in *P. putida* S12

The hmfT1 gene (formerly designated mfsl (Koopman et al., 2010a); SEQ ID NO: 7) was amplified from genomic DNA of *Cupriavidus basilensis* HMF14 by PCR using primers hmfT1(f) (SEQ ID NO: 13) and hmfT1(r) (SEQ ID NO: 14). The PCR product was introduced as a 1359-bp EcoRI-NheI fragment in pJNNmcs(t) yielding pJNNhmfT1(t). The hmfH gene (SEQ ID NO: 11) including its native ribosome binding site (RBS) was amplified by PCR from genomic DNA of *C. basilensis* HMF14 using primers FN23 (SEQ ID NO 15) and FN24 (SEQ ID NO: 16). The PCR product was cloned as a 1777-bp EcoRI fragment in pBT'mcs yielding plasmid pBT'hmfH. Plasmids pBT'hmfH and pJNNhmfT1(t) were successively introduced into *P. putida* S12, yielding *P. putida* S12_B38.

*P. putida* S12_B38 was cultured in fed-batches as described in the general methodology section. In the batch phase, a cell density of approximately 3 g CDW/l was achieved after which the glycerol feed and the HMF feed were started. A control fed-batch culture was performed with *P. putida* S12_2642 (similar to *P. putida* S12_hmfH (Koopman et al., 2010b)) which does not express HmfT1.

Figure 2A:
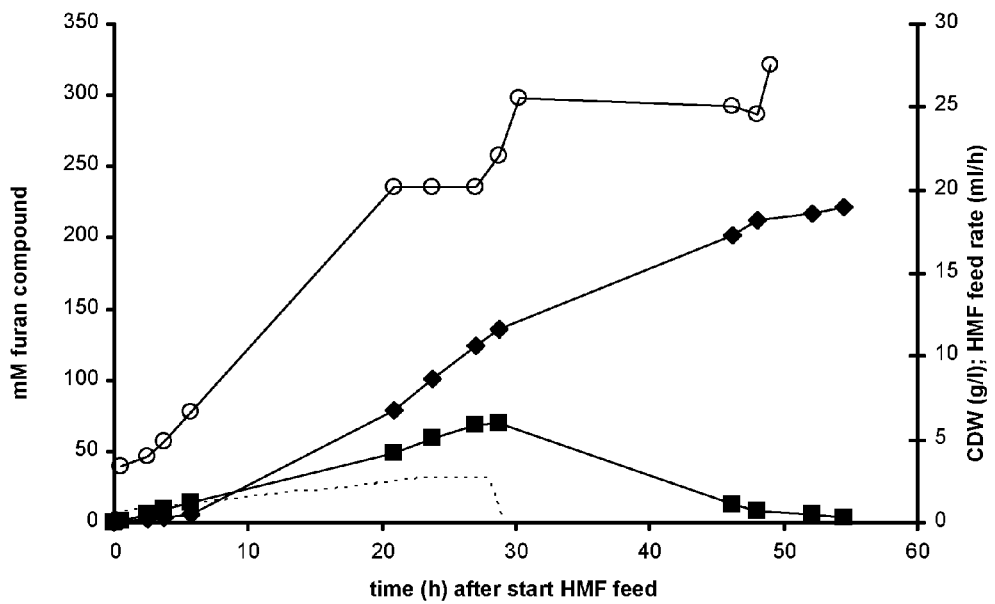
FIG. 2 discloses FDCA production and HMF-acid accumulation in HMF-fed cultures of *P. putida* S12_2642 (FIG. 2a) and B38 (FIG. 2b) (♦, FDCA (mM); ■, HMF-acid (mM); ○, cell dry weight (CDW; g/l); dotted line: HMF feed rate (ml 4 M solution/h))
Figure 2B:
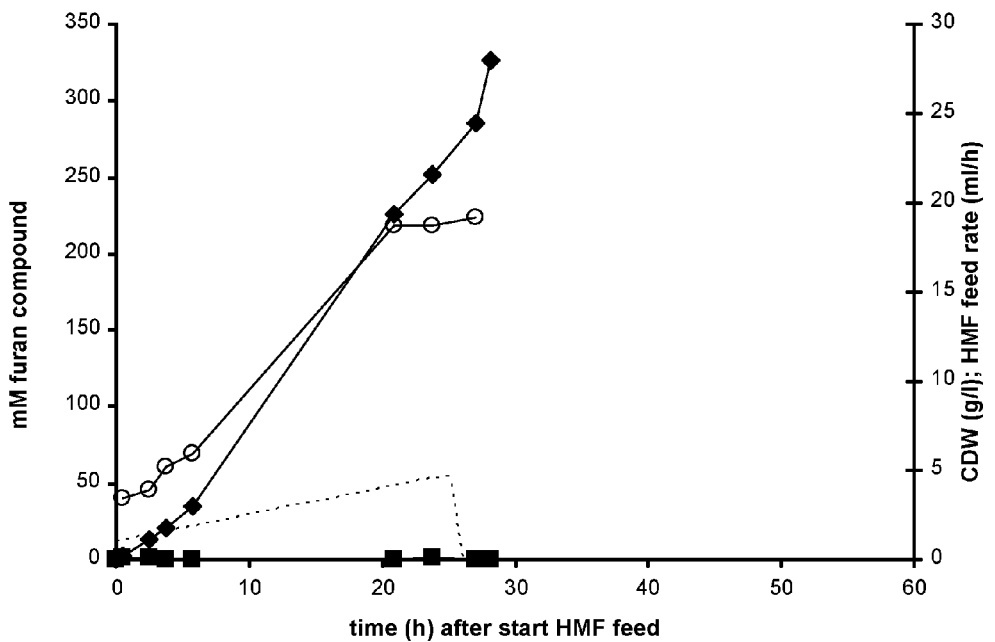
Figure 3:
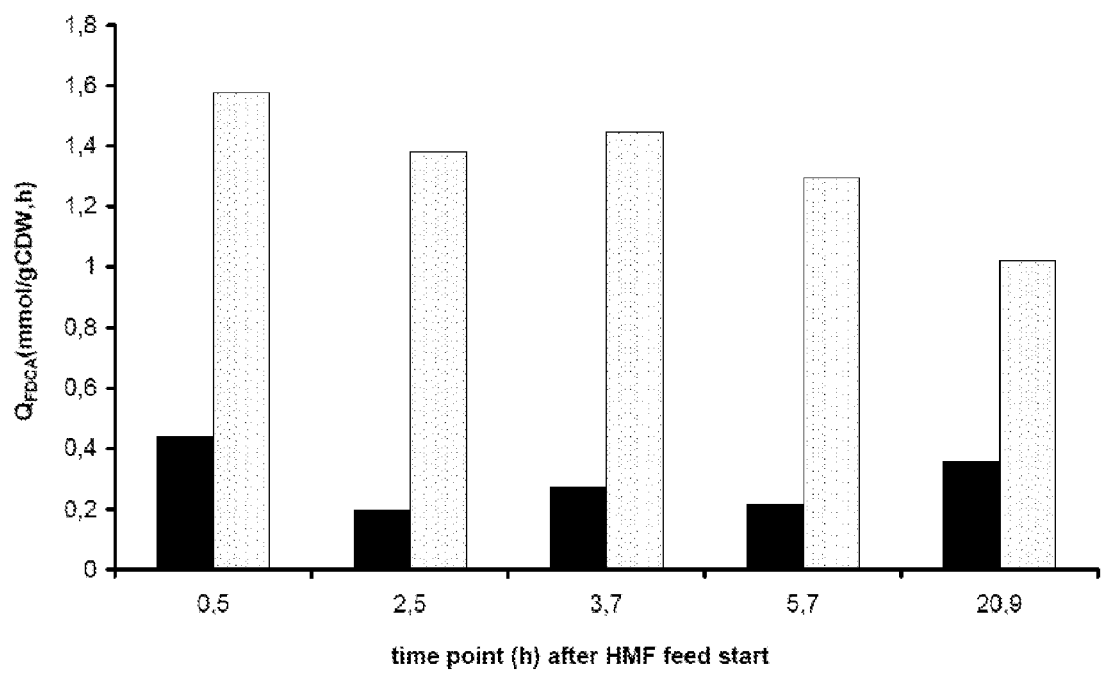
FIG. 3 discloses specific FDCA productivity at various time points during the fed-batch processes presented in FIG. 2 (Dark: *P. putida* S12_2642; Light: *P. putida* S12_B38).

FIG. 2 shows the concentrations of FDCA and HMF-acid in HMF-fed cultures of *P. putida* strains S12_2642 and S12_B38. The extensive accumulation of HMF-acid is evident for *P. putida* S12_2642. By contrast, the HMF-acid accumulation was negligible in the *P. putida* S12_B38 culture. The reduced HMF-acid accumulation furthermore allowed increased HMF feed rates, which resulted in higher FDCA titers in a considerably shorter process time. This was also clearly reflected in the specific FDCA productivity for the tested strains (FIG. 3).

Example II

Co-Expression of HmfH and a Polypeptide from *Methylobacterium radiotolerans* JCM 2831 Improves FDCA Production in *P. putida* S12

The gene with locus tag mrad2831_4728 (SEQ ID: 9) was amplified from genomic DNA of *Methylobacterium radiotolerans* JCM2831 by PCR using primers Mrad(f) (SEQ ID NO: 17) and Mrad(r) (SEQ ID NO: 18). The PCR product was introduced as a 1381-bp EcoRI-NheI fragment in pJNNmcs (t) yielding pJNN_Mrad(t). Plasmids pBT'hmfH (see Example I) and pJNN_Mrad(t) were successively introduced into *P. putida* S12, yielding *P. putida* S12_B51.

*P. putida*_B51 was cultured in shake flasks on mineral salts medium (4× buffer strength) supplemented with 1 g/l yeast extract, 80 mM glycerol, 2 mM glucose, 100 µM Na-salicylate, 50 µg/ml kanamycin and 10 µg/ml gentamicin. As control strain, *P. putida* S12_B38 was used (see Example I). After overnight culturing, the cultures were supplemented with 80 mM glycerol and 100 µM Na-salicylate. Subsequently, approximately 10 mM HMF was added and FDCA production was assessed.

Figure 4A:
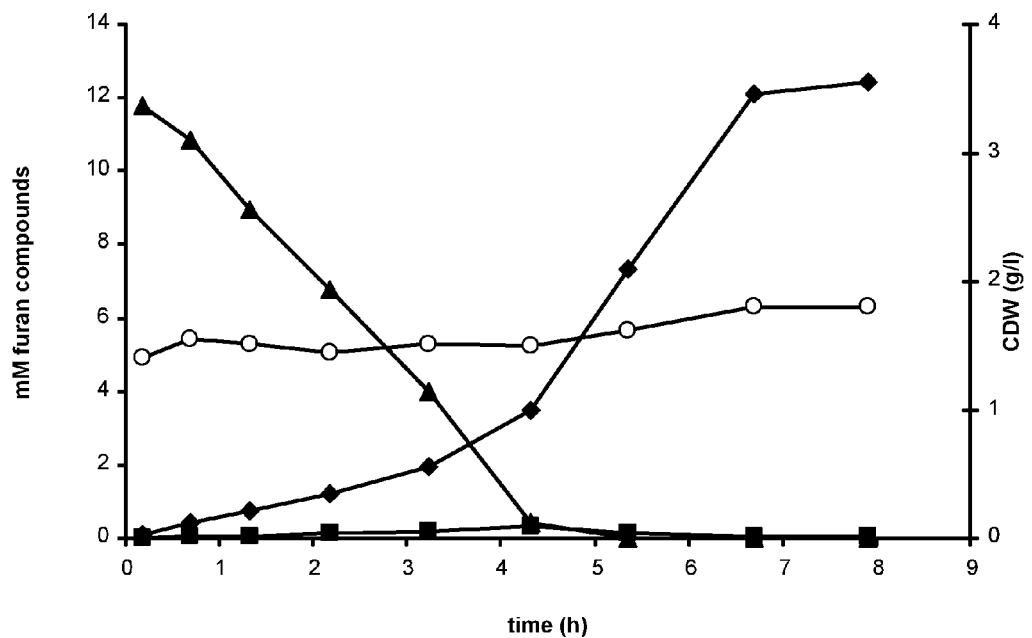
FIG. 4 discloses FDCA production and HMF-acid accumulation in shake-flask experiments with *P. putida* S12_B38 (FIG. 4a) and B51 (FIG. 4b) (▲, HMF (mM); ♦, FDCA (mM); ■, HMF-acid (mM); ○, cell dry weight (CDW; g/l))
Figure 4B:
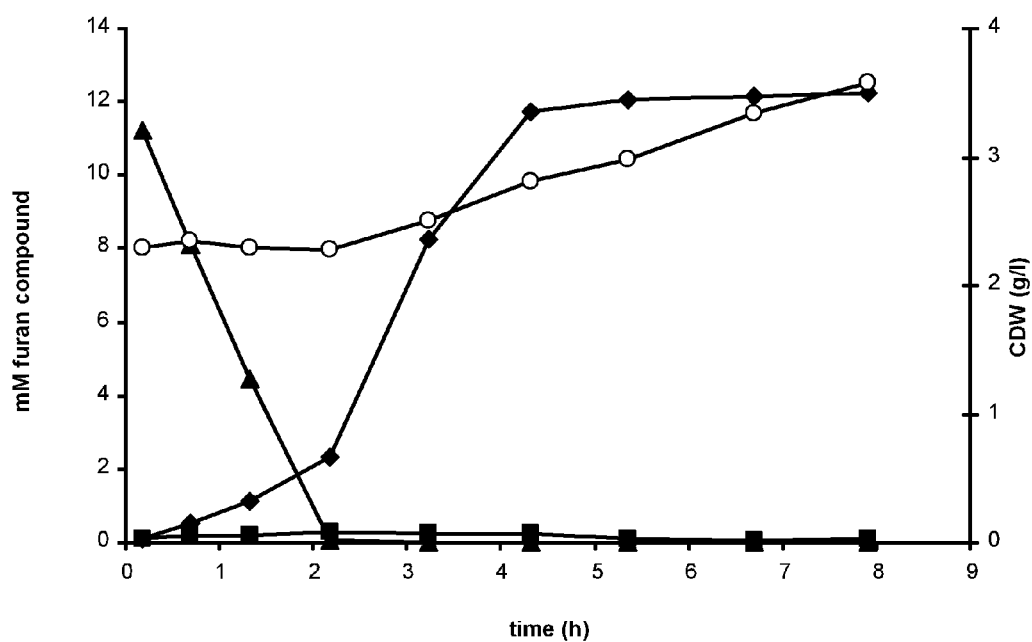

FIG. 4 shows that the HMF-acid accumulation during FDCA production was negligible for both strains, confirming that HmfT1 and the Mrad2831_4728 polypeptide exhibited a similar functionality. For *P. putida* S12_B38, the FDCA production showed a longer lag phase and a somewhat slower rate, which could be attributed to the lower initial biomass density (FIG. 4A). The specific maximum FDCA productivity, however, was identical for both strains, i.e., 2.36 mmol FDCA/(g CDW, h), indicating that the Mrad2831_4728 and HmfT1 polypeptides were equally effective in minimizing HMF-acid accumulation and maximizing FDCA production.

Example III

High-Level HMF-Acid Conversion Capacity by *P. putida* S12 Co-Expressing HmfH and HmfT1

As demonstrated in Example I, co-expression of HmfH and HmfT1 in *P. putida* S12 considerably improved the specific capacity to oxidize HMF to FDCA. To make optimal use of this improved capacity, a fed-batch experiment was performed with *P. putida* S12_B38 starting at a high biomass density.

Figure 5:
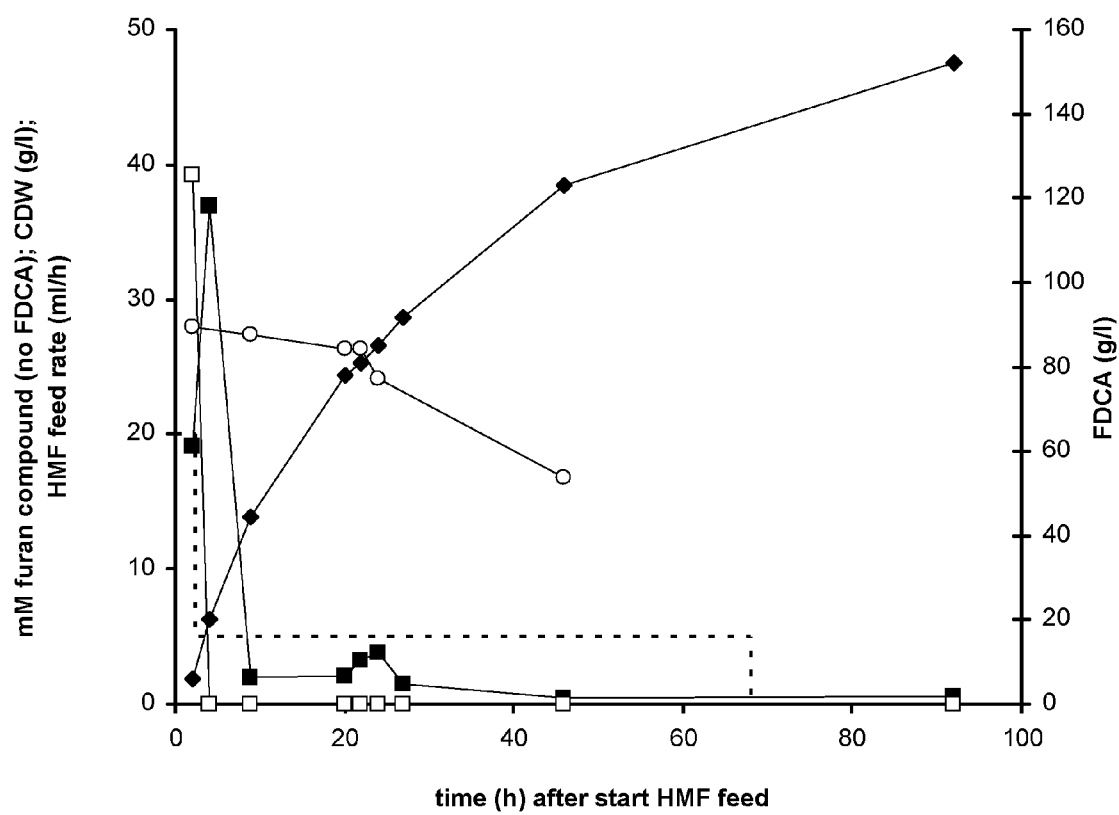
FIG. 5 discloses FDCA production and HMF-acid accumulation in HMF-fed high-cell density culture of *P. putida* S12_B38 starting at high cell density (□, HMF; ♦, FDCA (mM); ■, HMF-acid (mM); ○, cell dry weight (CDW; g/l); dotted line: HMF feed rate (ml 4 M solution/h)).

The HMF feed was started at a high rate (20 ml/h; 4 M HMF feed solution) in order to saturate the oxidation capacity of *P. putida* S12_B38 and provoke the accumulation of HMF and HMF-acid (FIG. 5). When HMF-acid had accumulated to approximately 20 mM, the HMF feed rate was lowered to 5 ml/h and the furanics concentrations were monitored. Initially, the HMF-acid concentration increased to approximately 37 mM due to oxidation of residual accumulated HMF, after which it dropped to less than 2 mM within 5 h, at an HMF feed rate of 0.72 mmol/(g CDW.h).

These results clearly demonstrate that the HMF-acid oxidation capacity was improved by co-expression of HmfH and HmfT1. The results by Koopman et al. (2010b), showed that *P. putida* S12_hmfH (which lacks HmfT1) required over 50 h to reduce the HMF-acid concentration from approximately 50 mM to less than 5 mM, at a much lower HMF feed rate (0.09 mmol/(g CDW.h)). The improved HMF-acid oxidation capacity resulted in a much higher final FDCA titer (152 g/l vs 30.1 g/l by Koopman et al. (2010b)) that was furthermore achieved in a shorter process time (94 h vs 115 h by Koopman et al. (2010b)).

Example IV

Co-Expression of HmfH, HmfT1 and an Aldehyde Dehydrogenase from *C. basilensis* HMF 14 Improves FDCA Production in *P. putida* S12

The gene encoding an aldehyde dehydrogenase (SEQ ID 26; translated amino acid sequence: SEQ ID 19) associated with the HMF-degradation operon in *Cupriavidus basilensis* HMF14 (Wierckx et al., 2011) was amplified by PCR using primers FN13 (SEQ ID 33) and FN14 (SEQ ID 34). The PCR product was introduced as a 1543-bp NotI fragment in Bsp120I-digested (compatible to NotI) pBT'hmfH (see example I) yielding pBT'hmfH-adh. The plasmid variant in which the aldehyde dehydrogenase encoding gene was present in the forward (f) orientation (pBT'hmfH-adh(f)) and pJNNhmfT1(t) (see example I) were successively introduced into *P. putida* S12. The resulting strain, *P. putida* S12_B97, co-expressed HmfH, HmfT1, and the aldehyde dehydrogenase. As a control strain for co-expression of the HmfH oxidoreductase and the aldehyde dehydrogenase (i.e., without the HMF-acid transporter HmfT1), *P. putida* S12_B101 was constructed which only contained pBT'hmfH-adh(f). *P. putida* S12_B38 (see example I) was used as control strain for co-expression of HmfT1 and HmfH without the aldehyde dehydrogenase.

*P. putida* strains S12_B38, S12_B97 and S12_B101 were cultured in shake flasks on mineral salts medium (4× buffer strength) supplemented with 1 g/l yeast extract, 80 mM glycerol, 2 mM glucose, 50 µg/ml kanamycin and 10 µg/ml gentamicin (note: for strain B101 only kanamycin was added). Na-salicylate (1 µM) was added for induction of hmfT1 in the precultures only. After addition of approximately 10 mM HMF, the accumulation of FDCA and HMF-acid was assessed.

Figure 6A:
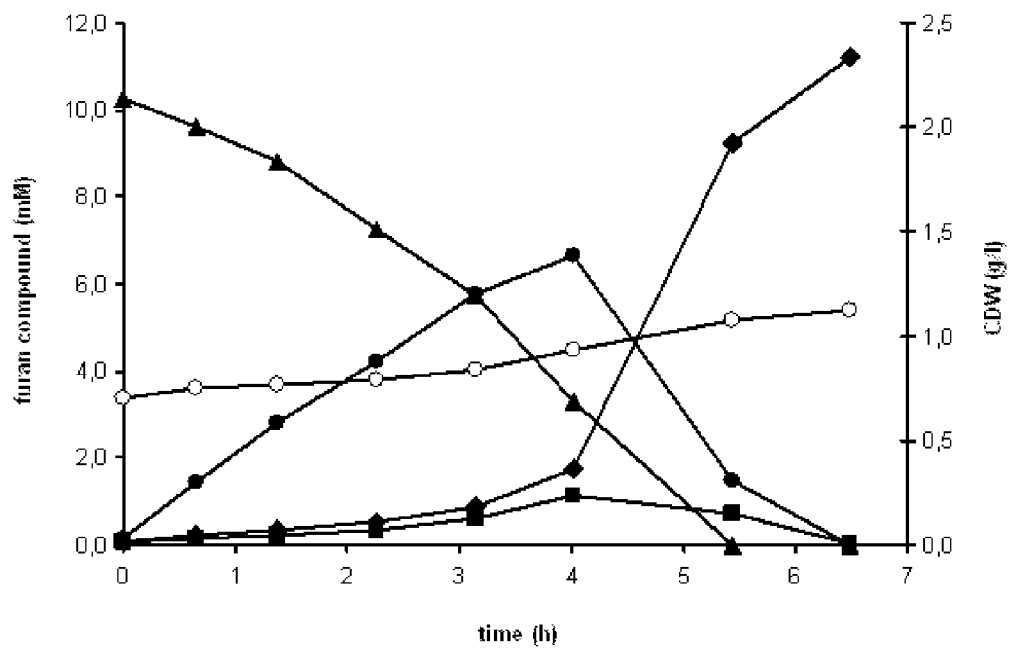
FIG. 6 discloses the accumulation of FDCA, FFA and HMF-acid in HMF containing shake-flask cultures of *P. putida* S12_B38 (co-expressed HmfH and HmfT1; A); S12_B97 (co-expressed HmfH, HmfT1 and aldehyde dehydrogenase; B); and S12_B101 (co-expressed HmfH and aldehyde dehydrogenase; C). ▲, HMF (mM); ♦, FDCA (mM); ■, HMF-acid (mM); ●, FFA (mM); ○, cell dry weight (CDW; g/l).
Figure 6B:
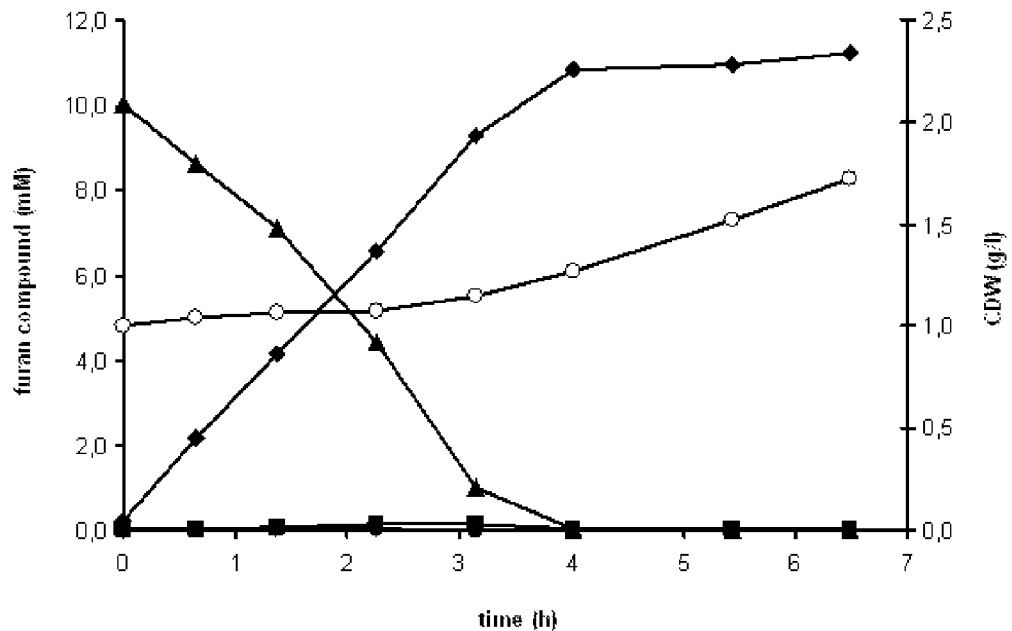
Figure 6C:
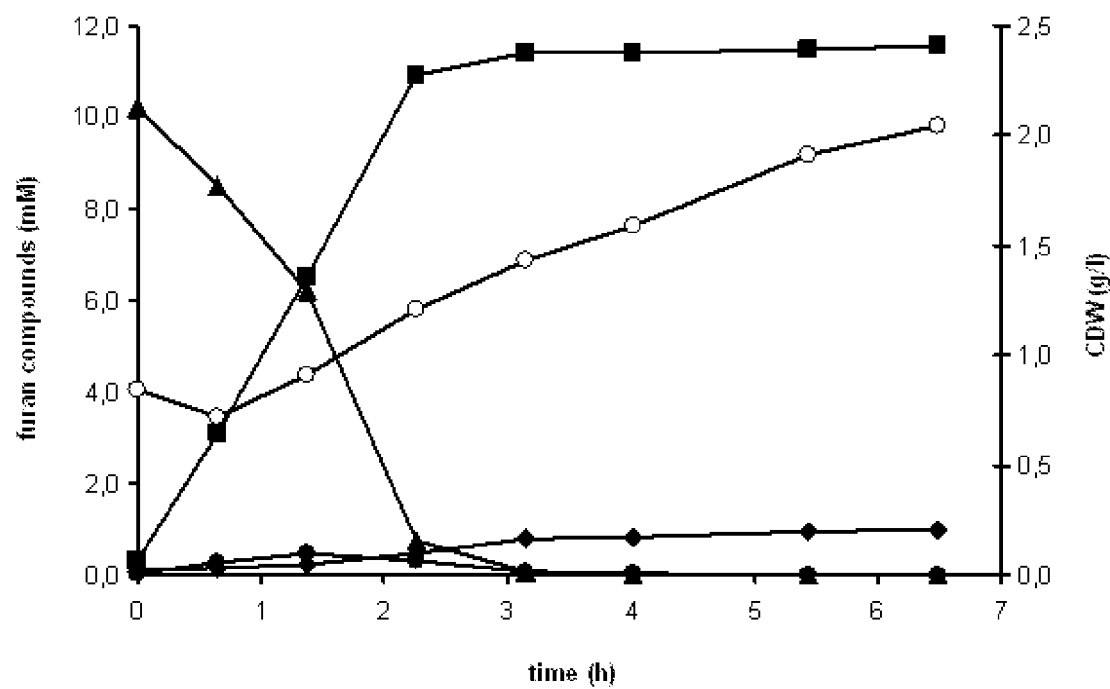

In the strain that co-expressed HmfH (oxidoreductase) and HmfT1 (HMF-acid transporter) (strain S12_B38; FIG. 6A), FDCA production only commenced after FFA had accumulated to a substantial level. HMF acid accumulated transiently to low amounts, as observed previously (see example II). When the aldehyde dehydrogenase was co-expressed with HmfH and HmfT1 (strain S12_B97; FIG. 6B), FDCA formation commenced without delay, and both FFA and HMF-acid were observed only in trace amounts. Co-expression of the aldehyde dehydrogenase and HmfH without HmfT1 (strain S12_B101; FIG. 6C), resulted in extensive accumulation of HMF-acid whereas only small amounts of FFA and FDCA were produced.

The results demonstrated that the oxidation of HMF to HMF-acid is significantly enhanced by expressing the aldehyde dehydrogenase. HmfT1 must be co-expressed, however, to enable efficient biotransformation of the HMF-acid produced. The aldehyde dehydrogenase furthermore improved the oxidation of the intermediate product FFA to FDCA. Thus, simultaneous expression of the aldehyde dehydrogenase and HmfT1 considerably improves the overall potential for, and rate of, HMF oxidation via HMF-acid to the final product.

REFERENCES

Almeida et al. (2009) Metabolic effects of furaldehydes and impacts on biotechnological processes. Applied Microbiology and Biotechnology, 82 (4): 625-638.

Altschul et al., (1997) Gapped BLAST and PSI-BLAST: a new generation of protein database search programs. Nucleic Acids Res, 25 (17): 3389-3402.

Altschul, et al., (1990) Basic local alignment search tool. J. Mol. Biol., 215: 403-10.

Ausubel et al. (eds.) (1995), Current Protocols in Molecular Biology, (John Wiley & Sons, N.Y.

Hawksworth et al., (1995) In: Ainsworth and Bisby's Dictionary of The Fungi, 8th edition, CAB International, University Press, Cambridge, UK.

Koopman et al., (2010a) Identification and characterization of the furfural and 5-(hydroxymethyl)furfural degradation pathways of *Cupriavidus basilensis* HMF14. PNAS (2010a), Vol. 107, p. 4919-4924.

Koopman et al., (2010b) Efficient whole-cell biotransformation of 5-(hydroxymethyl)furfural into FDCA, 2,5-furandicarboxylic acid. Bioresour. Technol. (2010b), Vol. 101, p. 6291-6296.

Meyers et al., (1988) Optimal alignments in linear space CABIOS, 4:11-17. Needleman et al., (1970) A general method applicable to the search for similarities in the amino acid sequences of two proteins. J. Mol. Biol. (48): 444-453.

Nichols N N, Mertens J A. Identification and transcriptional profiling of *Pseudomonas putida* genes involved in furoic acid metabolism (2008) FEMS Microbiol Lett 284: 52-57

Sambrook et al., (1989), Molecular Cloning, A Laboratory Manual, Cold Spring Harbor Press, N.Y.

Sambrook et al., (2001) Molecular cloning—a laboratory manual. Third edition. Cold Spring Harbor Laboratory Press, Cold Spring Harbor, N.Y.

Werpy et al., (2004) Top Value-Added Chemicals from Biomass, Volume I—Results of screening for potential Candidates from Sugars and Synthesis gas.

Wierckx et al., (2008) Transcriptome analysis of a phenol producing *Pseudomonas putida* S12 construct: genetic and physiological basis for improved production. J Bacteriol 190: 2822-2830.

Wierckx et al. (2010) Isolation and characterization of *Cupriavidus basilensis* HMF14 for biological removal of inhibitors from lignocellulosic hydrolysate. Microb Biotechnol 3: 336-343.

Wierckx et al., (2011) Microbial degradation of furanic compounds: biochemistry, genetics, and impact. Appl Microbiol Biotechnol 92:1095-1105

The invention claimed is:

1. An isolated cell that is genetically modified by the introduction of a first polynucleotide sequence coding for a polypeptide having 5-(hydroxymethyl)furan-2-carboxylic acid (HMF-acid) transport capabilities, wherein the first polynucleotide sequence has at least 95% sequence identity with SEQ ID NO: 7; and a second polynucleotide sequence coding for a polypeptide having HMF-acid oxidoreductase activity, wherein the polypeptide having HMF-acid oxidoreductase activity comprises an amino acid sequence having at least 95% sequence identity with at least one of SEQ ID NO: 5 and 6.

2. The genetically modified cell of claim 1, wherein the cell comprises a third polynucleotide sequence coding for a polypeptide having furanic aldehyde dehydrogenase activity.

3. The genetically modified cell of claim 2, wherein the polypeptide having furanic aldehyde dehydrogenase activity comprises an amino acid sequence having at least 95% sequence identity with at least one of SEQ ID NO: 19, 20, 21, 22, 23, 24 and 25.

4. The genetically modified cell of claim 1, wherein the cell is a bacterial cell, a yeast cell or a filamentous fungal cell.

5. The genetically modified cell of claim 2, wherein the cell is a bacterial cell, a yeast cell, or a filamentous fungal cell.

6. The genetically modified cell of claim 4, wherein the cell is selected from the group consisting of, the genera *Escherichia, Anabaena, Caulobacter, Gluconobacter, Rhodobacter, Pseudomonas, Paracoccus, Bacillus, Brevibacterium, Corynebacterium, Rhizobium, Sinorhizobium, Bradyrhizobium, Flavobacterium, Klebsiella, Enterobacter, Lactobacillus, Lactococcus, Methylobacterium, Staphylococcus, Streptomyces, Zymomonas, Acetobacter, Streptococcus, Bacteroides, Selenomonas, Megasphaera, Burkholderia, Cupriavidus, Ralstonia, Methylovorus, Rhodopseudomonas, Acidiphilium, Dinoroseobacter, Agrobacterium, Sulfolobus, Sphingomonas, Candida, Hansenula, Kluyveromyces, Pichia, Saccharomyces, Schizosaccharomyces, Yarrowia, Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Phanerochaete, Pleurotus, Schizophyllum, Talaromyces, Thermoascus, Thielavia, Tolypocladium* and *Trichoderma*.

7. The genetically modified cell of claim 5, wherein the cell is selected from the group consisting of the genera *Escherichia, Anabaena, Caulobacter, Gluconobacter, Rhodobacter, Pseudomonas, Paracoccus, Bacillus, Brevibacterium, Corynebacterium, Rhizobium, Sinorhizobium, Bradyrhizobium, Flavobacterium, Klebsiella, Enterobacter, Lactobacillus, Lactococcus, Methylobacterium, Staphylococcus, Streptomyces, Zymomonas, Acetobacter, Streptococcus, Bacteroides, Selenomonas, Megasphaera, Burkholderia, Cupriavidus, Ralstonia, Methylovorus, Rhodopseudomonas, Acidiphilium Dinoroseobacter, Agrobacterium, Sulfolobus, Sphingomonas, Candida, Hansenula, Kluyveromyces, Pichia, Saccharomyces, Schizosaccharomyces, Yarrowia, Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Phanerochaete, Pleurotus, Schizophyllum, Talaromyces, Thermoascus, Thielavia, Tolypocladium* and *Trichoderma*.

8. The genetically modified cell of claim 2, wherein the first and second polynucleotide sequence are located on a single vector.

9. A vector comprising a first polynucleotide sequence coding for a polypeptide having 5-(hydroxymethyl)furan-2-carboxylic acid (HMF-acid) transport capabilities, wherein the first polynucleotide sequence has at least 95% sequence identity with SEQ ID NO: 7; and a second polynucleotide sequence coding for a polypeptide having HMF-acid oxidoreductase activity, wherein the polypeptide having HMF-acid oxidoreductase activity comprises an amino acid sequence having at least 95% sequence identity with at least one of SEQ ID NO: 5 and 6.

10. The vector of claim 9, wherein the vector comprises a third polynucleotide sequence coding for a polypeptide having furanic aldehyde dehydrogenase activity.

11. The vector of claim 10, wherein the polypeptide having furanic aldehyde dehydrogenase activity comprises an amino acid sequence having at least 95% sequence identity with at least one of SEQ ID NO: 19, 20, 21, 22, 23, 24, or 25.

12. A process for oxidizing HMF-acid, the process comprising the step of incubating the cell of claim 1 in the presence of HMF-acid under conditions suitable for the oxidation of HMF-acid by said cell.

13. A process for producing 2,5-furandicarboxylic acid (FDCA), the process comprising the step of incubating the cell of claim 1 or claim 2 in the presence of one or more furanic precursors of HMF-acid under conditions suitable for the oxidation by said cell of the one or more furanic precursors to FDCA.

14. The process of claim 13, wherein the at least one furanic precursor is selected from the group consisting of 5-(hydroxymethyl)furan-2-carbaldehyde (HMF), furan-2,5-dicarbaldehyde (DFF), [5(hydroxymethyl)furan-2-yl]methanol (HMF alcohol).

15. The process of claim 14, wherein the furanic precursor is obtained from one or more hexose sugars.

16. The process of claim 15, wherein the furanic precursor is obtained from one or more hexose sugars by acid-catalyzed dehydration.

17. The process of claim 13, wherein FDCA is recovered from a reaction mixture by a process comprising acid precipitation followed by at least one of cooling crystallization and solvent extraction.

18. A genetically modified cell according to claim 1, capable of being used for biotransformation of furanic precursors to FDCA.

19. The genetically modified cell according to claim 18, wherein the furanic precursors are selected from the group consisting of 5-(hydroxymethyl)furan-2-carbaldehyde (HMF), [5-(hydroxymethyl)furan-2-yl]methanol (HMF alcohol), 5-(hydroxymethyl)furan-2-carboxylic acid (HMF-acid) furan-2,5-dicarbaldehyde (DFF) and 5-formylfuran-2-carboxylic acid (FFA).

20. The genetically modified cell of claim 6, wherein the cell is selected from the group consisting of the species *Bacillus subtilis, Bacillus amyloliquefaciens, Bacillus licheniformis, Bacillus puntis, Bacillus megaterium, Bacillus halodurans, Bacillus pumilus, Gluconobacter oxydans, Caulobacter crescentus, Methylobacterium extorquens, Methylobacterium radiotolerans, Methylobacterium nodulans, Rhodobacter sphaeroides, Pseudomonas zeaxanthinifaciens, Pseudomonas putida, Pseudomonas putida* S12, *Paracoccus denitrificans, Escherichia coli, Corynebacterium glutamicum, Staphylococcus carnosus, Streptomyces lividans, Sinorhizobium meliloti, Bradyrhizobium japonicum, Rhizobium radiobacter, Rhizobium leguminosarum, Rhizobium leguminosarum* bv. *trifolii, Agrobacterium radiobacter, Cupriaividus basilensis, Cupriavidus necator, Ralstonia eutropha, Ralstonia pickettii, Burkholderia phytofirmans, Burkholderia phymatum, Burkholderia xenovorans, Burkholderia graminis, Rhodopseudomonas palustris, Acidiphilium cryptum, Dinoroseobacter shibae, Sulfolobus acidocaldarius, Sulfolobus islandicus, Sulfolobus solfataricus, Sulfolobus tokodaii, Kluyveromyces lactis, Saccharomyces cerevisiae, Hansenula polymorpha, Yarrowia lipolytica, Pichia stipitis, Pichia pastoris, Aspergillus niger, Aspergillus awamori, Aspergillus foetidus, Aspergillus sojae, Aspergillus fumigatus, Talaromyces emersonii, Aspergillus oryzae, Chrysosporium lucknowense, Trichoderma reesei* and *Penicillium chrysogenum*.

21. The genetically modified cell of claim 7, wherein the cell is selected from the group consisting of the species *Bacillus subtilis, Bacillus amyloliquefaciens, Bacillus licheniformis, Bacillus puntis, Bacillus megaterium, Bacillus halodurans, Bacillus pumilus, Gluconobacter oxydans, Caulobacter crescentus, Methylobacterium extorquens, Methylobacterium radiotolerans, Methylobacterium nodulans, Rhodobacter sphaeroides, Pseudomonas zeaxanthinifaciens, Pseudomonas putida, Pseudomonas putida* S12, *Paracoccus denitrificans, Escherichia coli, Corynebacterium glutamicum, Staphylococcus carnosus, Streptomyces lividans, Sinorhizobium meliloti, Bradyrhizobium japonicum, Rhizobium radiobacter, Rhizobium leguminosarum, Rhizobium leguminosarum* bv. *trifolii, Agrobacterium radiobacter, Cupriaividus basilensis, Cupriavidus necator, Ralstonia eutropha, Ralstonia pickettii, Burkholderia phytofirmans, Burkholderia phymatum, Burkholderia xenovorans, Burkholderia graminis, Rhodopseudomonas palustris, Acidiphilium cryptum, Dinoroseobacter shibae, Sulfolobus acidocaldarius, Sulfolobus islandicus, Sulfolobus solfataricus, Sulfolobus tokodaii, Kluyveromyces lactis, Saccharomyces cerevisiae, Hansenula polymorpha, Yarrowia lipolytica, Pichia stipitis, Pichia pastoris, Aspergillus niger, Aspergillus awamori, Aspergillus foetidus, Aspergillus sojae, Aspergillus fumigatus, Talaromyces emersonii, Aspergillus oryzae, Chrysosporium lucknowense, Trichoderma reesei* and *Penicillium chrysogenum*.

22. The genetically modified cell of claim 8, wherein the vector further comprises the third polynucleotide sequence.

* * * * *

SEQUENCE LISTING

```
<160> NUMBER OF SEQ ID NOS: 34

<210> SEQ ID NO 1
<211> LENGTH: 441
<212> TYPE: PRT
<213> ORGANISM: Cupriavidus basilensis HMF14

<400> SEQUENCE: 1

Met Glu Ala Val Ala Lys Lys Arg Thr Glu Thr Ile Ser Glu Ala Leu
1               5                   10                  15

Pro Ala Ala Thr Asn Arg Gln Val Phe Gly Ala Val Thr Ala Ser Cys
            20                  25                  30
```

```
Met Gly Trp Ala Leu Asp Leu Phe Asp Leu Phe Ile Leu Leu Phe Val
             35                  40                  45
Ala Pro Val Ile Gly Arg Leu Phe Phe Pro Ser Glu His Ala Met Leu
 50                  55                  60
Ser Leu Ala Ala Val Tyr Ala Ser Phe Ala Val Thr Leu Leu Met Arg
 65                  70                  75                  80
Pro Leu Gly Ser Ala Ile Phe Gly Thr Tyr Ala Asp Arg His Gly Arg
                 85                  90                  95
Lys Gly Ala Met Val Val Ala Val Thr Gly Val Gly Leu Ser Thr Ala
                100                 105                 110
Ala Phe Gly Leu Leu Pro Thr Val Gly Gln Val Gly Leu Leu Ala Pro
            115                 120                 125
Ala Leu Phe Ile Leu Leu Arg Leu Val Gln Gly Ile Phe Val Gly Gly
            130                 135                 140
Val Val Ala Ser Thr His Thr Ile Gly Thr Glu Ser Val Pro Pro Ser
145                 150                 155                 160
Trp Arg Gly Ala Val Ser Gly Leu Val Gly Gly Gly Ala Gly Ile
                165                 170                 175
Gly Ala Leu Leu Ala Ser Ile Thr Tyr Met Ala Met Thr Ala Leu Phe
                180                 185                 190
Pro Gly Glu Ala Phe Asp Ala Trp Gly Trp Arg Cys Met Phe Phe Ser
            195                 200                 205
Gly Ile Ile Ser Ser Val Leu Gly Leu Phe Ile Phe Asn Ser Leu Glu
            210                 215                 220
Glu Ser Pro Leu Trp Lys Gln Leu Gln Ala Ala Lys Gly His Ala Ala
225                 230                 235                 240
Pro Val Glu Asn Pro Leu Arg Val Ile Phe Ser Arg Gln Tyr Arg Gly
                245                 250                 255
Val Leu Phe Val Asn Ile Leu Leu Thr Val Gly Gly Gly Ser Ala Tyr
                260                 265                 270
Tyr Leu Thr Ser Gly Tyr Leu Pro Thr Phe Leu Lys Val Val Lys
            275                 280                 285
Ala Pro Ala Gly Ala Ser Ala Ala Ile Leu Met Ala Ser Ser Val Gly
            290                 295                 300
Val Ile Val Ala Ser Ile Ile Ala Gly His Leu Ser Thr Leu Ile Gly
305                 310                 315                 320
Arg Lys Arg Ala Phe Leu Leu Ile Gly Ala Leu Asn Val Val Leu Leu
                325                 330                 335
Pro Leu Ile Tyr Gln Arg Met Pro Ala Ala Pro Asp Val Thr Thr Leu
                340                 345                 350
Gly Ile Tyr Ala Val Ala Leu Ala Met Leu Gly Ser Thr Gly Phe Ala
            355                 360                 365
Pro Ile Leu Ile Phe Leu Asn Glu Arg Val Ser His Gln His Pro Cys
            370                 375                 380
Tyr Gly Asn Trp Pro Val Met Glu Tyr Arg Leu Cys His Arg Arg His
385                 390                 395                 400
Asp Ala Thr Phe Ala Ser Leu Cys Ala Ala Pro Pro Arg Leu Pro Lys
                405                 410                 415
Cys Trp Gly Ser Arg Arg Gly Val Lys Ala Phe Thr Ala Gly Ala Ala
            420                 425                 430
Ile Val Trp Asn Ala Pro Leu Gly Glu
            435                 440
```

```
<210> SEQ ID NO 2
<211> LENGTH: 449
<212> TYPE: PRT
<213> ORGANISM: Cupriavidus basilensis HMF14

<400> SEQUENCE: 2
```

| Met | Glu | Ala | Val | Ala | Lys | Lys | Ser | Ala | Ala | Thr | Ile | Ser | Glu | Ala | Leu |
|---|---|---|---|---|---|---|---|---|---|---|---|---|---|---|---|
| 1 | | | | 5 | | | | | 10 | | | | | 15 | |

| Pro | Ala | Ala | Ser | Asn | Arg | Gln | Val | Phe | Gly | Ala | Val | Ala | Ala | Ser | Cys |
| | | | 20 | | | | | 25 | | | | | 30 | | |

| Met | Gly | Trp | Ala | Leu | Asp | Leu | Phe | Asp | Leu | Phe | Ile | Leu | Leu | Phe | Val |
| | | 35 | | | | | 40 | | | | | 45 | | | |

| Ala | Pro | Val | Ile | Gly | Arg | Leu | Phe | Phe | Pro | Ser | Glu | His | Ala | Met | Leu |
| | 50 | | | | | 55 | | | | | 60 | | | | |

| Ser | Leu | Ala | Ala | Val | Tyr | Ala | Ser | Phe | Ala | Val | Thr | Leu | Leu | Met | Arg |
| 65 | | | | | 70 | | | | | 75 | | | | | 80 |

| Pro | Leu | Gly | Ser | Ala | Ile | Phe | Gly | Ser | Tyr | Ala | Asp | Arg | His | Gly | Arg |
| | | | | 85 | | | | | 90 | | | | | 95 | |

| Lys | Gly | Ala | Met | Val | Val | Ala | Val | Thr | Gly | Val | Gly | Leu | Ser | Thr | Ala |
| | | | 100 | | | | | 105 | | | | | 110 | | |

| Ala | Phe | Gly | Leu | Leu | Pro | Thr | Val | Gly | Gln | Val | Gly | Leu | Leu | Ala | Pro |
| | | 115 | | | | | 120 | | | | | 125 | | | |

| Ala | Leu | Phe | Ile | Leu | Leu | Arg | Leu | Val | Gln | Gly | Ile | Phe | Val | Gly | Gly |
| | 130 | | | | | 135 | | | | | 140 | | | | |

| Val | Val | Ala | Ser | Thr | His | Thr | Ile | Gly | Thr | Glu | Ser | Val | Pro | Pro | Ser |
| 145 | | | | | 150 | | | | | 155 | | | | | 160 |

| Trp | Arg | Gly | Ala | Val | Ser | Gly | Leu | Val | Gly | Gly | Gly | Ala | Gly | Leu |
| | | | | 165 | | | | | 170 | | | | | 175 |

| Gly | Ala | Leu | Leu | Ala | Ser | Ile | Thr | Tyr | Met | Ala | Met | Thr | Ala | Leu | Phe |
| | | 180 | | | | | 185 | | | | | 190 | | | |

| Pro | Gly | Glu | Ala | Phe | Asp | Ala | Trp | Gly | Trp | Arg | Cys | Met | Phe | Phe | Ser |
| | | 195 | | | | | 200 | | | | | 205 | | | |

| Gly | Ile | Ile | Ser | Ser | Val | Leu | Gly | Leu | Phe | Ile | Phe | Asn | Ser | Leu | Glu |
| | | 210 | | | | | 215 | | | | | 220 | | | |

| Glu | Ser | Pro | Leu | Trp | Lys | Gln | Leu | Gln | Ala | Ala | Lys | Gly | His | Ala | Ala |
| 225 | | | | | 230 | | | | | 235 | | | | | 240 |

| Pro | Val | Glu | Asn | Pro | Leu | Arg | Val | Ile | Phe | Ser | Arg | Gln | Tyr | Arg | Gly |
| | | | | 245 | | | | | 250 | | | | | 255 | |

| Val | Leu | Phe | Val | Asn | Ile | Leu | Leu | Thr | Val | Gly | Gly | Gly | Ser | Ala | Tyr |
| | | | 260 | | | | | 265 | | | | | 270 | | |

| Tyr | Leu | Thr | Ser | Gly | Tyr | Leu | Pro | Thr | Phe | Leu | Lys | Val | Val | Val | Lys |
| | | 275 | | | | | 280 | | | | | 285 | | | |

| Ala | Ser | Ala | Gly | Glu | Ser | Ala | Ala | Ile | Leu | Met | Ala | Ser | Ser | Leu | Gly |
| | 290 | | | | | 295 | | | | | 300 | | | | |

| Val | Ile | Val | Ala | Ser | Ile | Leu | Ala | Gly | His | Leu | Ser | Thr | Met | Ile | Gly |
| 305 | | | | | 310 | | | | | 315 | | | | | 320 |

| Arg | Lys | Arg | Ala | Phe | Leu | Leu | Ile | Gly | Ala | Leu | Asn | Val | Val | Leu |
| | | | | 325 | | | | | 330 | | | | | 335 |

| Pro | Leu | Leu | Tyr | Gln | Trp | Met | Pro | Ala | Ala | Pro | Asp | Thr | Thr | Thr | Leu |
| | | | 340 | | | | | 345 | | | | | 350 | | |

| Gly | Leu | Tyr | Ala | Val | Val | Leu | Ser | Met | Leu | Gly | Cys | Ser | Gly | Phe | Ala |
| | | 355 | | | | | 360 | | | | | 365 | | | |

| Pro | Ile | Leu | Ile | Phe | Leu | Asn | Glu | Arg | Phe | Pro | Thr | Ser | Ile | Arg | Ala |
| | | 370 | | | | | 375 | | | | | 380 | | | |

```
Thr Gly Thr Gly Leu Ser Trp Asn Ile Gly Phe Ala Val Gly Gly Met
385                 390                 395                 400

Met Pro Thr Phe Ala Ser Leu Cys Ala Ser Thr Pro Ala Glu Leu Pro
                405                 410                 415

Met Val Leu Gly Ile Phe Leu Ala Val Val Thr Ile Ile Tyr Leu Val
                420                 425                 430

Gly Ala Phe Ile Val Pro Glu Thr Val Gly Arg Leu Gly Asp Asn Gly
            435                 440                 445

Ala
```

<210> SEQ ID NO 3
<211> LENGTH: 449
<212> TYPE: PRT
<213> ORGANISM: Methylobacterium radiotolerans JCM2831

<400> SEQUENCE: 3

```
Met Gln Thr Ala Ala Thr Phe Ala Ser Asp Pro Pro Ala Leu Ala Lys
1               5                   10                  15

Pro Thr Gly Arg Gln Thr Val Thr Ala Ala Met Ala Ser Leu Phe Gly
                20                  25                  30

Trp Gly Leu Asp Leu Phe Asp Leu Phe Ile Leu Leu Tyr Val Ala Pro
            35                  40                  45

Val Val Gly Thr Leu Phe Phe Pro Ala Asp Lys Pro Met Leu Ser Leu
        50                  55                  60

Ala Gly Ala Tyr Ala Ser Phe Ala Val Thr Leu Leu Ile Arg Pro Leu
65                  70                  75                  80

Gly Ser Ala Leu Phe Gly Ser Tyr Ala Asp Arg Phe Gly Arg Arg Arg
                85                  90                  95

Ala Leu Met Val Ala Val Gly Val Gly Ile Ser Thr Ala Val Phe
                100                 105                 110

Gly Leu Leu Pro Thr Val Gly Gln Ile Gly Trp Leu Ala Thr Ala Val
            115                 120                 125

Phe Leu Phe Phe Arg Leu Val Gln Gly Ile Phe Val Gly Gly Val Val
        130                 135                 140

Ala Ala Ser His Thr Ile Gly Thr Glu Ser Val Pro Glu Arg Trp Arg
145                 150                 155                 160

Gly Leu Met Ser Gly Ala Val Gly Gly Gly Ser Ala Ile Gly Gly
                165                 170                 175

Leu Leu Ala Ser Leu Val Phe Tyr Val Val Ser Leu Met Ala Pro Gly
            180                 185                 190

Glu Ala Phe Ala Glu Trp Gly Trp Arg Leu Met Phe Phe Ser Gly Leu
        195                 200                 205

Leu Thr Ser Val Ile Gly Leu Ile Leu Phe Arg Asn Leu Glu Glu Ser
        210                 215                 220

Pro Ile Phe Lys Glu Leu Gln Ala Arg Lys Ala Ala Leu Arg Ala Gly
225                 230                 235                 240

Ala Pro Ala Glu Ala Ser Pro Ile Arg Ser Leu Phe Ser Pro Ser Asn
                245                 250                 255

Arg Gly Ser Phe Ala Val Ala Thr Leu Ile Ser Phe Gly Gly Ala
                260                 265                 270

Ala Tyr Tyr Leu Thr Ser Gly Tyr Leu Pro Thr Leu Leu Lys Leu Val
            275                 280                 285

Asn Gly Val Pro Asn Ala Thr Ala Ser Met Ile Leu Ile Gly Ala Asn
        290                 295                 300
```

```
Val Ala Ala Ala Ile Gly Ala Cys Gly Met Gly Glu Leu Ser Gln His
305                 310                 315                 320

Ile Gly Arg Lys Arg Ser Phe Leu Leu Met Gly Val Ile Arg Leu Leu
            325                 330                 335

Ala Phe Pro Ala Leu Phe Leu Thr Met Ala Asn Thr Thr Ser Leu Val
            340                 345                 350

Gly Val Ala Ala Cys Ala Phe Leu Leu Ala Leu Ile Ala Asn Gly Ser
            355                 360                 365

Tyr Gly Pro Leu Leu Ile Phe Leu Asn Glu Lys Phe Pro Thr Ala Val
            370                 375                 380

Arg Ala Thr Gly Thr Gly Leu Thr Trp Asn Ile Gly Phe Ala Leu Gly
385                 390                 395                 400

Gly Met Leu Pro Thr Leu Val Ser Leu Val Ala Asp Gly Pro Thr Gln
            405                 410                 415

Ile Pro Met Val Leu Ala Val Ile Thr Thr Gly Val Thr Leu Val Tyr
            420                 425                 430

Leu Val Gly Ala Phe Leu Thr Asp Glu Thr Gln Gly Asn Leu Asp Arg
            435                 440                 445

Ala

<210> SEQ ID NO 4
<211> LENGTH: 443
<212> TYPE: PRT
<213> ORGANISM: Sulfolobus acidocaldarius DSM 639

<400> SEQUENCE: 4

Met Lys Lys Glu Glu Lys Phe Thr Ser Asn His Phe Lys Trp Thr Leu
1               5                   10                  15

Ala Thr Phe Phe Thr Trp Thr Phe Asp Leu Tyr Asp Leu Phe Thr Ile
            20                  25                  30

Leu Leu Val Ala Pro Tyr Ile Ser Ser Leu Phe Phe Pro Ser Ser Ile
            35                  40                  45

Thr Phe Leu Ser Ile Ala Ala Thr Tyr Ala Gly Phe Ala Thr Ser Leu
50                  55                  60

Ile Met Arg Pro Val Gly Ala Thr Val Phe Gly Ser Val Ser Asp
65                  70                  75                  80

Lys Val Gly Arg Lys Arg Ala Ile Phe Tyr Gly Leu Ile Gly Leu Val
            85                  90                  95

Ile Thr Ser Thr Leu Gln Gly Ala Leu Pro Thr Tyr Gln Val Val Gly
            100                 105                 110

Val Ile Ala Pro Ile Leu Leu Leu Ala Val Arg Leu Ile Gln Gly Val
            115                 120                 125

Phe Ile Gly Gly Ile Thr Ala Gly Ser His Val Ile Gly Pro Glu Ser
            130                 135                 140

Val Pro Glu Arg Tyr Arg Gly Ile Val Gly Gly Leu Gly Phe Ser Ala
145                 150                 155                 160

Ala Gly Val Ala Tyr Leu Ile Ala Ala Gly Trp Phe Phe Leu Thr Thr
            165                 170                 175

Ile Leu Tyr Pro Gly Ser Ser Tyr Leu Val Trp Gly Trp Arg Val Met
            180                 185                 190

Phe Phe Gly Gly Leu Leu Ser Leu Ala Val Leu Gly Phe Val Asn Tyr
            195                 200                 205

Leu Val Pro Glu Ser Glu Val Trp Thr Lys Ile Lys Lys Arg Gly Ser
            210                 215                 220
```

```
Val Val Lys Ser Pro Leu Lys Glu Ile Phe Ser Lys Tyr Arg Tyr Gln
225                 230                 235                 240

Leu Gly Val Ala Leu Leu Leu Ser Ile Gly Trp Gly Ala Ser Phe Tyr
            245                 250                 255

Val Thr Asp Gly Ile Leu Pro Thr Phe Leu Ser Ser Val Asn Lys Leu
            260                 265                 270

Ala Lys Thr Glu Ile Ala Ile Val Met Ile Ile Gly Ser Ile Gly Met
        275                 280                 285

Ser Ile Gly Pro Leu Ile Gly Gly Glu Ile Ser Gln Ile Ile Gly Arg
    290                 295                 300

Lys Ile Thr Ser Leu Ile Gly Ala Ile Ile Val Leu Ala Val Val Gly
305                 310                 315                 320

Pro Leu Phe Leu Ser Leu Gly Ser Leu Lys Ser Gly Asp Leu Asn Gln
            325                 330                 335

Ile Ile Leu His Ser Phe Ala Ile Leu Phe Leu Val Asp Ile Gly Gly
            340                 345                 350

Gly Met Leu Met Thr Tyr Leu Asn Glu Ile Tyr Pro Ala Ser Val Arg
        355                 360                 365

Gly Thr Gly Val Gly Phe Thr Trp Asn Thr Gly Phe Ala Ile Gly Gly
    370                 375                 380

Thr Ile Pro Thr Ile Ile Ser Leu Ala Val Ala Ser Ala Gly Leu Ser
385                 390                 395                 400

Ala Phe Pro Ser Ile Met Phe Tyr Thr Leu Ile Val Val Ser Val Ile
            405                 410                 415

Ile Leu Val Gly Thr Val Leu Thr Lys Glu Thr Lys Gly Thr Ile Ser
            420                 425                 430

Lys Glu Glu Tyr Glu Ile Gln Lys Glu Thr Leu
        435                 440

<210> SEQ ID NO 5
<211> LENGTH: 579
<212> TYPE: PRT
<213> ORGANISM: Cupriavidus basilensis HMF14

<400> SEQUENCE: 5

Met Asp Thr Pro Arg Glu Arg Phe Asp Tyr Val Ile Val Gly Gly Gly
1               5                   10                  15

Ser Ala Gly Cys Val Leu Ala Asn Arg Leu Ser Gln Asp Pro Ala Ile
            20                  25                  30

Arg Val Ala Leu Ile Glu Ala Gly Val Asp Thr Pro Pro Asp Ala Val
        35                  40                  45

Pro Ala Glu Ile Leu Asp Ser Tyr Pro Met Pro Leu Phe Phe Gly Asp
    50                  55                  60

Arg Tyr Ile Trp Pro Ser Leu Gln Ala Arg Val Ala Gly Gly Arg
65                  70                  75                  80

Ser Lys Val Tyr Glu Gln Gly Arg Val Met Gly Gly Ser Ser Ile
            85                  90                  95

Asn Val Gln Ala Ala Asn Arg Gly Leu Pro Arg Asp Tyr Asp Glu Trp
            100                 105                 110

Ala Ala Ser Gly Ala Ser Gly Trp Ser Trp Gln Asp Val Leu Pro Tyr
        115                 120                 125

Phe Arg His Leu Glu Arg Asp Val Asp Tyr Gly Asn Ser Pro Leu His
    130                 135                 140

Gly Ser His Gly Pro Val Pro Ile Arg Arg Ile Leu Pro Gln Ala Trp
145                 150                 155                 160
```

```
Pro Pro Phe Cys Thr Glu Phe Ala His Ala Met Gly Arg Ser Gly Leu
            165                 170                 175

Ser Ala Leu Ala Asp Gln Asn Ala Glu Phe Gly Asp Gly Trp Phe Pro
            180                 185                 190

Ala Ala Phe Ser Asn Leu Asp Asp Lys Arg Val Ser Thr Ala Ile Ala
            195                 200                 205

Tyr Leu Asp Ala Asp Thr Arg Arg Ala Asn Leu Arg Ile Tyr Ala
            210                 215                 220

Glu Thr Thr Val Arg Lys Leu Val Val Ser Gly Arg Glu Ala Arg Gly
225                 230                 235                 240

Val Ile Ala Met Arg Ala Asp Gly Ser Arg Leu Ala Leu Asp Ala Gly
            245                 250                 255

Glu Val Ile Val Ser Ala Gly Ala Leu Gln Ser Pro Ala Ile Leu Met
            260                 265                 270

Arg Ala Gly Ile Gly Asp Ala Gly Ala Leu Gln Ala Leu Gly Ile Glu
            275                 280                 285

Val Val Ala Asp Arg Pro Gly Val Gly Arg Asn Leu Gln Asp His Pro
            290                 295                 300

Ala Leu Thr Phe Cys Gln Phe Leu Ala Pro Gln Tyr Arg Met Pro Leu
305                 310                 315                 320

Ser Arg Arg Arg Ala Ser Met Thr Ala Ala Arg Phe Ser Ser Gly Val
            325                 330                 335

Pro Gly Gly Glu Ala Ser Asp Met Tyr Leu Ser Ser Ser Thr Arg Ala
            340                 345                 350

Gly Trp His Ala Leu Gly Asn Arg Leu Gly Leu Phe Phe Leu Trp Cys
            355                 360                 365

Asn Arg Pro Phe Ser Arg Gly Gln Val Ser Leu Ala Gly Ala Gln Pro
            370                 375                 380

Asp Val Pro Pro Met Val Glu Leu Asn Leu Leu Asp Asp Glu Arg Asp
385                 390                 395                 400

Leu Arg Arg Met Val Ala Gly Val Arg Lys Leu Val Gln Ile Val Gly
            405                 410                 415

Ala Ser Ala Leu His Gln His Pro Gly Asp Phe Phe Pro Ala Thr Phe
            420                 425                 430

Ser Pro Arg Val Lys Ala Leu Ser Arg Val Ser Arg Gly Asn Val Leu
            435                 440                 445

Leu Thr Glu Leu Leu Gly Ala Val Leu Asp Val Ser Gly Pro Leu Arg
            450                 455                 460

Arg Ser Leu Ile Ala Arg Phe Val Thr Gly Gly Ala Asn Leu Ala Ser
465                 470                 475                 480

Leu Leu Thr Asp Glu Ser Ala Leu Glu Gly Phe Val Arg Gln Ser Val
            485                 490                 495

Phe Gly Val Trp His Ala Ser Gly Thr Cys Arg Met Gly Ala His Ala
            500                 505                 510

Asp Arg Ser Ala Val Thr Asp Ala Ala Gly Arg Val His Asp Val Gly
            515                 520                 525

Arg Leu Arg Val Ile Asp Ala Ser Leu Met Pro Arg Leu Pro Thr Ala
            530                 535                 540

Asn Thr Asn Ile Pro Thr Ile Met Leu Ala Glu Lys Ile Ala Asp Thr
545                 550                 555                 560

Met Gln Ala Glu Arg Arg Ala Val Arg Pro Ala Ser Ser Glu Val Ala
            565                 570                 575
```

His Pro Ser

<210> SEQ ID NO 6
<211> LENGTH: 564
<212> TYPE: PRT
<213> ORGANISM: Bradyrhizobium japonicum USDA 110

<400> SEQUENCE: 6

Met Tyr Asp Tyr Ile Ile Val Gly Gly Ser Ala Gly Ser Val Leu
1               5                   10                  15

Ala His Arg Leu Ser Ala Lys Ser Ala Asn Lys Val Leu Leu Cys Glu
            20                  25                  30

Ala Gly Gln Asp Thr Pro Pro Gly Asn Glu Pro Ala Gly Ile Arg Asp
        35                  40                  45

Ser Tyr Pro Gly Thr Ala Tyr Phe Asp Pro Arg Phe His Trp Thr Glu
    50                  55                  60

Leu Lys Val Thr Thr Gln Val Val Ser His Asn Asn Pro Thr Glu Ala
65                  70                  75                  80

Arg Pro Pro Leu Arg Lys Tyr Glu Gln Ala Arg Val Leu Gly Gly Gly
                85                  90                  95

Ser Ser Ile Asn Gly Gln Met Ala Asn Arg Gly Ala Pro Thr Asp Tyr
            100                 105                 110

Asp Glu Trp Asp Ala Arg Gly Ala Glu Gly Trp Thr Trp Asn Asp Val
        115                 120                 125

Leu Pro Phe Phe Lys Lys Val Glu Arg Asp Leu Asp Phe Asp Gly Pro
    130                 135                 140

Tyr His Gly Lys Asp Gly Arg Ile Pro Val Arg Arg Ile Pro Arg Glu
145                 150                 155                 160

His Trp Thr Arg His Ser Gln Ala Phe Ala Asp Ala Phe Gln Gln Ala
                165                 170                 175

Gly His Gln Phe Val Ala Asp Gln Asn Gly Glu Phe Val Asp Gly Tyr
            180                 185                 190

Phe Ala Val Thr His Ser Asn Gln Ala Glu Gln Arg Val Ser Ala Ala
        195                 200                 205

Met Gly Tyr Leu Asp Arg Asp Thr Arg Lys Arg Ala Asn Leu Thr Ile
    210                 215                 220

Ser Thr Asn Thr Gln Val Arg Glu Leu Leu Phe Glu Gly Thr Gln Cys
225                 230                 235                 240

Val Gly Val Lys Ala Arg Val Asp Gly Arg Glu Gln Glu Phe Arg Gly
                245                 250                 255

Arg Glu Ile Ile Leu Ser Ser Gly Ala Ile His Ser Pro Ala His Leu
            260                 265                 270

Leu Arg Ala Gly Ile Gly Pro Val Gly His Leu Lys Asp Met Gly Ile
        275                 280                 285

Pro Val Leu Thr Gly Leu Pro Gly Val Gly Gln Arg Leu Met Asp His
    290                 295                 300

Pro Ser Ile Ser Leu Ser Ser Phe Val Arg Arg Gly Ala Arg Met Asn
305                 310                 315                 320

Glu His Thr Arg Arg His Met Gln Leu Gly Leu Arg Tyr Ser Ser Gly
                325                 330                 335

Leu Ser Gly Val Pro Lys Gly Asp Met Phe Val Val Leu Ser Lys
            340                 345                 350

Ser Ala Trp His Ala Val Gly Ala Gln Ile Gly Ser Leu Leu Thr Phe
        355                 360                 365

```
Val Asn Lys Thr Tyr Ser Glu Thr Gly Gln Val Lys Leu Ala Ser Arg
    370                 375                 380

Asp Pro Ser Ala Glu Pro Ile Val Glu Phe Asn Leu Leu Ser Asp Arg
385                 390                 395                 400

Arg Asp Leu Asp Arg Leu Met Ser Gly Phe Arg Lys Met Ala Ala Val
                405                 410                 415

Gln Met Ser Glu Ile Val Arg Lys Val Thr Asp Lys Pro Phe Pro Ala
            420                 425                 430

Ala Tyr Thr Asp Lys Val Arg Lys Ile Gly Val Val Asn Thr Gly Asn
                435                 440                 445

Lys Ile Leu Thr Arg Val Ala Ala Ala Leu Met Asp Gly Pro Ala Ala
450                 455                 460

Leu Arg His Tyr Leu Ile Asp Asn Phe Val Val Glu Gly Phe Thr Phe
465                 470                 475                 480

Asp Asp Val Met Asn Asp Glu Ala Leu Glu Ala Phe Val Arg Lys
                485                 490                 495

Ala Thr Ile Gly Val Trp His Ala Ser Cys Ser Cys Arg Met Gly Arg
                500                 505                 510

Ala Asp Asp Pro Met Ala Val Val Asp Asn Gln Gly Arg Val Arg Gly
                515                 520                 525

Val Gln Gly Leu Arg Val Val Asp Ala Ser Ile Phe Pro Val Val Pro
                530                 535                 540

Cys Ala Asn Thr Asn Phe Pro Val Leu Met Ser Ala Glu Lys Ile Ala
545                 550                 555                 560

Ala Thr Met Gln

<210> SEQ ID NO 7
<211> LENGTH: 1326
<212> TYPE: DNA
<213> ORGANISM: Cupriavidus basilensis HMF14

<400> SEQUENCE: 7
atggaagccg tagcaaagaa gcgtacagag acgatcagcg aggcgctgcc agcggcgacc      60
aatcgccagg tgtttggtgc cgtgacggcg tcgtgcatgg gatgggcgct ggacctgttc     120
gacctgttca tcctgctgtt cgtggcgccc gtgatcggca ggctgttttt cccgtcggag     180
cacgccatgc tgtcgctggc ggcggtgtat cgtcgtttg ccgtgacgct gctgatgcgg      240
ccgctcggct cggcgatctt cggcacttat gccgaccgcc acggccgcaa gggggcgatg     300
gtagttgccg tcactggcgt tggcttgtcc acggcggcgt tcggcctgct gcctacggtg     360
ggtcaggtgg ggctgcttgc gccagccttg tttatcctgc tgcggctggt gcagggcatc     420
ttcgtaggtg gcgtggtggc atccacccac accatcggta ccgaatcggt gccccgtcc      480 tggcgcggcg ccgtctccgg gctggtcggt ggcggtggcg cgggcatcgg ggcactgctg     540
gcttccatta cctacatggc gatgaccgcg ctgtttccgg gggaagcgtt cgatgcctgg     600
ggttggcgct gcatgttctt ctccggcatc atcagctcgg tgctcggcct gttcatcttc     660
aactcgctgg aggagtctcc gctgtggaag cagttgcagg cggccaaggg gcacgccgcg     720
ccggttgaga cccgctgcg cgtgatcttc cccgccagt accgtggcgt cctcttcgtc       780
aacatcctgc tcaccgtggg cggtggcagc gcctactacc tgacctccgg ctatctgccg     840
accttcctca aggtggtggt gaaggcaccg ctggcgcat ccgcagccat cctgatggcc      900
agcagtgttg gcgttatcgt ggcatcgata attgccggtc acctcagcac gctgattggt     960
cgcaagcgag ccttcctgct gatcggcgcc ttgaacgtgg tgctgctgcc gttgatctac    1020
```

```
caacggatgc cgcggcgcc ggatgtcacc acgcttggca tttatgccgt ggcgctggcg   1080
atgctgggca gcaccggctt cgccccgatc ctcattttcc tgaacgaacg ggtttcccac   1140
cagcatccgt gctacgggaa ctggcctgtc atggaatatc ggctttgcca tcggcggcat   1200
gatgcgacgt ttgcgtcgct gtgcgcagca ccccgcgac tgccaaagtg ctggggatct    1260
cgtcgcggtg tcaaagcatt tactgccggt gcggcgatcg tctggaacgc cgcgctgggg   1320
gagtga                                                              1326
```

<210> SEQ ID NO 8
<211> LENGTH: 1350
<212> TYPE: DNA
<213> ORGANISM: Cupriavidus basilensis HMF14

<400> SEQUENCE: 8

```
atggaagccg tagcaaagaa gagtgcagcg acgatcagcg aggcgctgcc agcggcgagc     60
aatcgccagg tgtttggtgc cgtggcggcg tcgtgcatgg gatgggcgct ggacctgttc    120
gacctgttca tcctgctgtt cgtggcgccc gtgatcggca ggctgttttt cccgtcggag   180
cacgcgatgc tgtcgctggc ggcggtgtat gcgtcgtttg ccgtgacgct gctgatgcgg   240
ccgctcggct cggcgatctt cggctcttat gccgaccgcc acggccgcaa gggggcgatg   300
gtggttgccg tcactggcgt tggcttgtcc acggcggcgt tcggcctgct gccgacggtg   360
ggtcaggtgg ggctgcttgc gccagccttg tttatcctgc tgcggctggt gcagggcatc   420
ttcgtgggtg gcgtggtggc atccacccac accatcggta ccgaatcggt gccccgtcc    480 tggcgcggcg ccgtttccgg gctggttggt ggcggtggcg cgggtctcgg ggcgctgctg   540
gcttccatta cctacatggc gatgaccgcg ctgtttccgg gggaagcgtt cgatgcctgg   600
ggttggcgct gcatgttctt ctccggcatc atcagctcgg tgctcggcct gttcatcttc   660
aactcgctgg aggagtctcc gctgtggaag cagttgcagg cggccaaggg gcacgccgcg   720
ccggttgaga acccgctgcg cgtgatcttc tcccgccagt accgtggtgt cctcttcgtc   780
aacatcctgc tcaccgtggg cggtggcagc gcctactacc tgacctccgg ctatctgccg   840
accttcctca aggtggtggt gaaggcatcg gctggcgagt ctgccgccat cctgatggcc   900
agcagtctgg gtgtgatcgt ggcatcgatt cttgccggcc acctcagtac gatgatcggc   960
cgcaagcgag ccttcctgtt gatcggcgcg ctgaacgtgg tagtactgcc gctgctctac   1020
cagtggatgc cggcggcgcc ggacaccacc acgctcggcc tgtatgctgt ggtgctgtcc   1080
atgctgggct gcagcggctt cgccccgatc ctcattttcc tgaacgaacg gttcccacc    1140 agcatccgtg ccacggggac cggcctgtca tggaatatcg gatttgccgt cggtggcatg   1200
atgccgacgt ttgcttcgct gtgcgccagc acccctgccg aactgccat ggtgctgggc    1260 atcttcctgg cggttgtcac catcatctac ctggtgggtg cgttcatcgt tccggagacg   1320
gtagggcgcc ttggcgacaa tggagcgtag                                    1350
```

<210> SEQ ID NO 9
<211> LENGTH: 1350
<212> TYPE: DNA
<213> ORGANISM: Methylobacterium radiotolerans JCM2831

<400> SEQUENCE: 9

```
atgcagaccg ccgccacctt cgcatccgat cccccgccc tcgccaaacc cacaggccgg     60
cagacggtga ccgccgccat ggcctcgctg ttcggctggg ggctcgatct cttcgacctg    120
```

| | |
|---|---|
| ttcatcctgc tttacgtcgc gccggtcgtt ggcacgttgt tcttcccggc ggacaagccg | 180 |
| atgctgtcgc tggccggcgc ctatgcgtcc ttcgcggtca cgctgctgat ccggcccctc | 240 |
| ggctcggccc tgttcggctc ctatgcggac cgcttcggcc gccgtcgcgc cctcatggtg | 300 |
| gcggtggtcg gcgtcggcat atcgaccgcg gtcttcggtc cctgccgac ggtcggccag | 360 |
| atcggatggc tcgcgactgc ggtcttcctt ttcttccgcc tcgtccaggg catcttcgtc | 420 |
| ggcggcgtcg tcgcggcatc ccacacgatc gggacggaat ccgtcccgga gcggtggcgg | 480 |
| gggctgatgt ccggggcggt cggcggtggc ggctcggcca tcggcggcct gcttgcctcc | 540 |
| ctggtcttct atgtcgtctc gctcatggcg ccggggagaag ccttcgccga gtggggctgg | 600 |
| cggctgatgt tcttctcggg tctcctgacc tcggtgatcg gcctgatcct cttccgcaat | 660 |
| ctcgaggaat ccccgatctt caaggaactg caggcccgga aggcggcgct ccgggcaggc | 720 |
| gctccggcgg aggcctcacc gatccgctcc ctgttctcac cgtccaaccg gggaagcttc | 780 |
| gcggtcgcga ctctcatctc cttcggtggt ggcgcagcct actaccttac gtccggctac | 840 |
| ctgccgaccc tcctcaagct cgtgaacggc gtgccgaacg ccaccgcctc gatgatcctg | 900 |
| atcggcgcca acgtcgcggc ggcgatcggc gcctgcggca tgggcgaact gagccagcat | 960 |
| atcgggcgca acggtcgtt ccttctgatg ggcgtcatcc gcctgctcgc ttttcccgcc | 1020 |
| ctgttcctga ccatggcgaa cacgacgagc ctcgttgggg tcgcggcctg cgccttcctg | 1080 |
| ctggcgctca tcgccaacgg cagctacggg ccgctgctga tcttcctcaa cgaaaaattc | 1140 |
| ccgacggcgg tgcgggccac ggggacgggc ctgacctgga acatcggctt cgcgctgggc | 1200 |
| ggcatgctgc cgacgctcgt ctcccttgtc gccgacgggc cgacgcaaat tccgatggtg | 1260 |
| ctggccgtca tcacgaccgg cgtcaccctg gtctatcttg tcggtgcctt cctgaccgac | 1320 |
| gagacgcagg gcaatctcga ccgggcctga | 1350 |

<210> SEQ ID NO 10
<211> LENGTH: 1332
<212> TYPE: DNA
<213> ORGANISM: Sulfolobus acidocaldarius DSM 639

<400> SEQUENCE: 10

| | |
|---|---|
| atgaaaaaag aagaaaaatt tacttcaaat cattttaaat ggactttagc aaccttttc | 60 |
| acctggacat tcgacttata tgacctgttc actatcctac ttgttgcacc ttatatctct | 120 |
| tccctgtttt tccccttcaag tatcactttc ttgtctatag cggcaacata tgcggggttt | 180 |
| gccacctcat tgatcatgag acctgtaggt gctacagtct ttgggtctag gtatcggac | 240 |
| aaggtaggta gaaagagggc tatttttttac ggtctaatag gtcttgtgat aacttccaca | 300 |
| ttacagggcg cattaccgac ttatcaagta gtaggagtga tagcaccaat attactgtta | 360 |
| gcagtgagac tgattcaagg ggtgttcata ggaggcataa ctgcaggtag tcatgtgata | 420 |
| ggacctgagt ctgtcccaga gaggtataga gggattgtag gtggactagg gttttcagct | 480 |
| gctggagtgg catacctcat agcagctggc tggttttcc tgacaaccat actctaccct | 540 |
| ggaagttcct atctggtatg gggatggaga gtgatgttct tggcgggct actgagctta | 600 |
| gctgtacttg gatttgtaaa ctatttagtc cctgagtctg aggtttggac taaaattaaa | 660 |
| aagagagggt cagtggtgaa gtctcccctc aaggagatat tttcgaaata caggtatcag | 720 |
| ttaggcgttg cactgctact ttcaattggc tggggtgcaa gttttttacgt tactgatggt | 780 |
| atactaccta cgttttttaag tagtgtcaat aaaattagcca agactgaaat agcaatagta | 840 |
| atgataatag ggtcaattgg gatgtcgata ggaccattaa taggagggga gatatcccag | 900 |

-continued

```
ataataggga ggaagataac gtcattaata ggtgcaatta ttgtactagc agtagttgga    960
cctctctttc tctccctggg ttcactaaaa tccggtgacc ttaatcagat aattcttcac   1020
tcttttgcaa tcctgttctt agtcgatata ggaggaggga tgctaatgac ttacctaaat   1080
gagatatatc cagctagcgt gaggggaaca ggggttggct tcacgtggaa tactgggttt   1140
gcaataggag ggacaatccc aaccataatc agcctagcag tagcttcagc aggtctctct   1200
gcttttccct ctataatgtt ctacaccttA atagtggtct ctgtaataat attagtgggt   1260
acagtactca cgaaggagac taagggtacc atatcaaagg aggagtatga gattcagaag   1320
gagactttat ag                                                      1332
```

<210> SEQ ID NO 11
<211> LENGTH: 1740
<212> TYPE: DNA
<213> ORGANISM: Cupriavidus basilensis HMF14

<400> SEQUENCE: 11

```
atggatacgc cgagggagcg tttcgactac gtgattgttg gcggcgggtc cgccggttgc     60
gtactggcca atcgcctgtc gcaggacccg gccatccgcg tcgcgctgat cgaggcgggc    120
gtcgatacgc cgccggacgc tgtgccggcg agatcctcg acagctatcc gatgcccttg    180
ttcttcggtg accggtatat ctggccatcg ctgcaagccc gcgccgtggc agggggcagg    240
tccaaggtct acgagcaagg gcgcgtcatg ggcggcggct ccagcatcaa cgtgcaggcg    300
gcaaaccgcg gctgccgcg cgactacgat gagtgggccg cgtcgggcgc gtccggatgg    360
tcgtggcagg atgtgctgcc gtatttccgc caccttgagc gcgatgtgga ttacggcaac    420
agcccgctgc acggcagcca cggaccggtg ccgatccgcc gcatcctgcc gcaggcttgg    480
ccgccgttct gcacggagtt tgcgcacgcg atgggccgca gcggcttgtc cgcgctggcc    540
gaccagaacg cggagttcgg cgatggctgg tttccggccg ccttctcgaa cctggatgac    600
aagcgggttt cgaccgccat cgcctatctc gacgcggata cgcgccggcg ggccaatctg    660
cggatctatg ccgagacaac ggtgcgcaag ctcgtcgtat ccggccggga agcgcgtggg    720
gtgatcgcca tgcgggccga tgggtcgcgg ctggcgctgg acgccgggga ggtcatcgtg    780
tccgcgggcg ccttgcagtc gcccgccatc ctgatgcgcg cggggatcgg cgacgccggc    840
gcgctgcagg ccctcggcat cgaggtcgta ccgaccgac ccggcgttgg ccgcaatctc    900
caggatcatc ccgcgctgac gttctgccag ttcctcgcgc ccagtaccg catgccgctc    960 tcgcgccggc gcgctagcat gacgcggcg cggttctcat cggggggtgcc aggtggcgag   1020 gcgtcggaca tgtacctgtc cagttccaca cgggcaggct ggcatgcact cggtaatcgg   1080
ctcggcctct tcttcctgtg gtgcaatcgg ccattctcgc gcgggcaggt gagccttgcg   1140
ggagcccagc cggatgtgcc gcccatggtg gagctcaacc tgctcgacga cgagcgggat   1200
ctgcggcgca tggtggccgg cgtacgcaag ttggtgcaga tcgtgggtgc gtcggccttg   1260
catcagcatc ccggtgattt cttccccgct acgttttcgc cgcgcgtcaa ggcgctgagc   1320
cgcgtgagcc gcggcaatgt gttgctcacg gagttgctgg gggcagtgct tgatgtctcg   1380
gggccgctgc gcagaagcct gatcgcgcgc tttgtcacgg gcggcgcaaa cctgccagc    1440 ctgctgacgg atgagtccgc gctagagggc ttcgtgcgcc agagcgtctt cggggtctgg   1500
catgccagcg gcacttgccg gatgggcgcg catgcggacc ggagcgcggt gacggatgcg   1560
gcgggccgcg ttcacgatgt tggcaggctg cgcgttattg acgcctctct gatgccgcgg   1620
```

| ctgccgacgg ccaataccaa catccccacc atcatgctcg cggaaaagat tgccgacacc | 1680 |
| atgcaagccg agcgccgcgc ggtccggccg gcatcgagcg aagttgccca tccgagttga | 1740 |

<210> SEQ ID NO 12
<211> LENGTH: 1695
<212> TYPE: DNA
<213> ORGANISM: Bradyrhizobium japonicum USDA 110

<400> SEQUENCE: 12

| gtgtacgact acattatcgt gggcggcggc tcggcggggt ccgtgctggc ccaccggctc | 60 |
| tccgcaaaga gtgccaacaa ggtcctgctc tgcgaagccg acaggacac accacccggc | 120 |
| aacgagccgg ccgagatcag ggacagctat ccgggcacgg cctatttcga tccgcgcttc | 180 |
| cactggacgg aattgaaggt cacgacgcag gtcgtcagcc acaacaatcc gaccgaagcg | 240 |
| cgtcctccct tgcgcaaata cgagcaggcg cgcgtgctcg gcggcggctc gtcgatcaac | 300 |
| ggccagatgg ccaaccgcgg cgcgccgacc gactacgacg aatgggatgc gcggggtgcc | 360 |
| gaagggtgga cgtggaacga cgtgctgccg ttcttcaaga aggtcgagcg cgacctcgat | 420 |
| ttcgacggcc cgtatcacgg caaggacggc cggatcccgg tgcgccggat tccgcgggag | 480 |
| cactggacac ggcattcgca ggccttcgcc gatgccttcc agcaggccgg tcatcaattc | 540 |
| gtggcggacc agaacggcga gttcgtcgac ggctatttcg cggtgacgca ctccaaccag | 600 |
| gccgagcagc gcgtctccgc cgcgatgggc tatctcgatc gcgacacccg caagcgcgcc | 660 |
| aacctcacga tctccaccaa cacgcaagtt cgggagctgc tgttcgaagg cacgcaatgc | 720 |
| gtcggcgtga aggccagggt cgacgggcgg gagcaggaat ccgcggacg cgagatcatt | 780 |
| ctctccagcg gcgccatcca ttcgccggcg catctgctcc gcgccggtat cggcccggtc | 840 |
| ggccacctca aggacatggg gattcccgtg ctgacgggct gccgggcgt cggccagcgc | 900 |
| ctgatggatc atccctcgat ttcgctgtcg tcctttgtcc gccgcggcgc gcgcatgaac | 960 |
| gagcatacca ggcgccacat gcagcttggc ctgcgctatt cgtccgggct gtcaggggtg | 1020 |
| ccgaagggcg acatgttcgt cgtcgtgctc agcaaatcgg cctggcacgc ggtcggcgcg | 1080 |
| caaatcggct cgctgctgac cttcgtcaac aagacctatt ccgagaccgg acaggtcaag | 1140 |
| cttgcctcgc gcgacccttc cgcagagccg atcgtcgagt tcaacctgct gtcggaccgg | 1200 |
| cgcgacctcg atcggctgat gagcggcttc gcaagatgg cggcggtgca gatgagcgaa | 1260 |
| atcgtcagga aggtgacgga caagccgttc ccggccgcct ataccgacaa ggtccgcaag | 1320 |
| atcggcgtgg tcaacaccgg gaacaagatc ctgaccagag tcgcggcggc gctcatggac | 1380 |
| gggccggcgg cgctgcgtca ctatctgatc gacaatttcg tggtcgaagg cttcaccttc | 1440 |
| gatgacgtga tgaacgacga cgaggcgctt gaagccttcg tgcgcaaggc gaccatcggc | 1500 |
| gtgtggcacg cctcgtgctc atgccgcatg ggccggccg acgatccgat ggcggtggtc | 1560 |
| gacaaccagg gccgcgtcag gggtgtccag ggtctgcggg tcgtcgacgc ctcgatcttc | 1620 |
| ccggtggtgc catgcgccaa caccaacttt ccggtgctga tgtcggcaga aagatcgct | 1680 |
| gcaaccatgc agtga | 1695 |

<210> SEQ ID NO 13
<211> LENGTH: 28
<212> TYPE: DNA
<213> ORGANISM: Artificial Sequence
<220> FEATURE:
<223> OTHER INFORMATION: Synthetic

<400> SEQUENCE: 13

```
                                    -continued acgaattcaa aggagacaac aatggaag                                          28

<210> SEQ ID NO 14
<211> LENGTH: 27
<212> TYPE: DNA
<213> ORGANISM: Artificial Sequence
<220> FEATURE:
<223> OTHER INFORMATION: Synthetic

<400> SEQUENCE: 14
aagctagctg agcagtcacc ctcactc                                           27

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
cggaattcca catgacaagg gagaccg                                           27

<210> SEQ ID NO 16
<211> LENGTH: 30
<212> TYPE: DNA
<213> ORGANISM: Artificial Sequence
<220> FEATURE:
<223> OTHER INFORMATION: Synthetic

<400> SEQUENCE: 16
cggaattcgc ttcggtcttc aactcggatg                                        30

<210> SEQ ID NO 17
<211> LENGTH: 28
<212> TYPE: DNA
<213> ORGANISM: Artificial Sequence
<220> FEATURE:
<223> OTHER INFORMATION: Synthetic

<400> SEQUENCE: 17
acgaattcgg aggaaatcta tgcagacc                                          28

<210> SEQ ID NO 18
<211> LENGTH: 26
<212> TYPE: DNA
<213> ORGANISM: Artificial Sequence
<220> FEATURE:
<223> OTHER INFORMATION: Synthetic

<400> SEQUENCE: 18
aagctagcgc agaaccgtat cgtcag                                            26

<210> SEQ ID NO 19
<211> LENGTH: 500
<212> TYPE: PRT
<213> ORGANISM: Cupriavidus basilensis HMF14

<400> SEQUENCE: 19

Met Asn Ala Gln His Trp Ile Ala Gly Ala Trp Thr Gly Glu Pro Ser
1               5                   10                  15

Ala Asp Ser Val Asn Pro Ala Asp Gly Thr Leu Ile Gly Gln Phe Ala
            20                  25                  30

Asp Gly Gly Thr Trp Gln Ala Glu Ala Ala Ile Ala Ala Ala Arg His
        35                  40                  45
```

-continued

```
Val Phe Glu Arg Thr Thr Trp Gly Gln Asp Ala Arg Leu Arg Gln Asp
    50                  55                  60

Val Leu Leu Ala Trp Ala Gly Ala Leu Glu Ala Glu Arg Glu Arg Leu
65                  70                  75                  80

Ala Ser Leu Leu Thr Ala Glu Asn Gly Lys Pro Val Ala Gln Ala Arg
                85                  90                  95

Gly Glu Val Gly Ala Ala Ile Ser Glu Val Arg Tyr Tyr Ala Gly Leu
            100                 105                 110

Ala Arg His Ile Pro Gly His Val Leu Glu Pro Glu Pro Gly Thr Ile
        115                 120                 125

Ser Thr Ile Leu Arg Glu Pro Ala Gly Val Ala Ala Ile Ile Val Pro
    130                 135                 140

Trp Asn Ala Pro Ala Val Leu Leu Val Arg Ser Leu Ala Pro Ala Leu
145                 150                 155                 160

Ala Ala Gly Cys Thr Ala Val Val Lys Ser Ala Ala Gln Thr Thr Leu
                165                 170                 175

Phe Thr Ala Ala Met Leu Arg Leu Phe Glu Arg Thr Ala Leu Pro Ala
            180                 185                 190

Gly Ala Val Asn Leu Val Cys Glu Thr Gly Tyr Ala Ala Ala Asp His
        195                 200                 205

Leu Val Arg Ser Arg Asp Val Asp Val Val Ser Phe Thr Gly Ser Thr
    210                 215                 220

Ala Thr Gly Lys Lys Ile Met Ile Ala Ala Asp Ser Val Lys Lys
225                 230                 235                 240

Leu Ser Leu Glu Leu Gly Gly Lys Ser Cys Cys Leu Val Phe Asp Asp
                245                 250                 255

Val Asp Ala Gln Ala Val Ala Lys Arg Leu Ala Leu Ala Ala Thr Val
            260                 265                 270

Ile Ser Gly Gln Gln Cys Thr Ala Ala Arg Arg Val Leu Val His Glu
        275                 280                 285

Ala Ile Ala Pro Gln Met Arg Arg His Leu Thr Glu Ala Leu Ala Ala
    290                 295                 300

Leu Arg Leu Gly Pro Gly Ile Glu Pro Asp Thr Gln Ile Gly Pro Leu
305                 310                 315                 320

Ile Asp His Pro Thr Arg Ala Met Val Ser Ala Gln Val Glu Arg Ala
                325                 330                 335

Cys Asp Glu Ala Asp Thr Val Leu Leu Arg Gly Thr Met Pro Gly Gly
            340                 345                 350

Ala Leu Ala Arg Gly Ala Phe Leu Ser Pro Thr Leu Val Glu His Ser
        355                 360                 365

Asp Pro Gly Ala Phe Phe Cys Gln Glu Glu Ile Phe Gly Pro Phe Val
    370                 375                 380

Thr Phe Glu Thr Phe Ala Thr Glu Asp Glu Ala Leu Ala Lys Ala Asn
385                 390                 395                 400

Asn Thr Val Phe Gly Leu Ser Ala Ser Val Trp Thr His His Gly Glu
                405                 410                 415

Arg Ala Ile Arg Leu Ala Arg Ala Leu Arg Asn Gly Thr Val Trp Val
            420                 425                 430

Asn Asp His Asn Arg Leu Phe Ala Glu Ala Glu Thr Gly Gly Tyr Arg
        435                 440                 445

Gln Ser Gly Leu Gly Arg Leu His Gly Tyr Asp Ala Leu Ala Asp Phe
    450                 455                 460
```

```
Thr Glu Leu Lys His Ile Cys Ile Gln Ala Gly Leu Pro Lys Gly Met
465                 470                 475                 480

Ser Gln Ala Gly Cys Arg Leu Ser Gly Val Ala Ala Arg Glu Arg Met
            485                 490                 495

Gly Val Ser Val
            500

<210> SEQ ID NO 20
<211> LENGTH: 479
<212> TYPE: PRT
<213> ORGANISM: Burkholderia sp. CCGE1002

<400> SEQUENCE: 20

Met Asn Ala Arg His Trp Ile Ala Gly Glu Trp Thr Gly Thr Pro Asn
1               5                   10                  15

Ile Asp Ser Ile Asp Pro Ala Thr Gly Asp Ala Ile Gly Arg Phe Ala
            20                  25                  30

Asp Gly Gly Ser Ser Glu Ala Asp Ala Ala Ile Ala Ala Ala Arg His
        35                  40                  45

Ala Phe Asp Arg Thr Thr Trp Ala Gln Asp Ala Arg Leu Arg Gln Asp
50                  55                  60

Val Leu Leu Gly Trp Ala Ser Ala Leu Glu Ala Glu Arg Asp Met Leu
65                  70                  75                  80

Ala Thr Leu Leu Thr Arg Glu Asn Gly Lys Ala Ile Ala Gln Ser Arg
                85                  90                  95

Asp Glu Ile Ala Gly Ala Ile Ser Glu Val Arg Tyr Tyr Ala Gly Leu
            100                 105                 110

Ala Arg His Ile Ala Gly His Val Leu Glu Pro Glu Pro Gly Thr Ile
        115                 120                 125

Ser Thr Met Leu Arg Glu Ala Ala Gly Val Ala Ala Ile Ile Val Pro
130                 135                 140

Trp Asn Ala Pro Ala Val Leu Leu Val Arg Ser Leu Ala Pro Ala Leu
145                 150                 155                 160

Ala Ala Gly Cys Thr Val Ile Val Lys Pro Ala Ala Gln Thr Ser Leu
                165                 170                 175

Leu Thr Ala Ala Met Leu Arg Cys Phe Glu His Thr Ala Leu Pro Glu
            180                 185                 190

Gly Ala Val Asn Leu Val Asn Glu Arg Gly Tyr Ala Ala Ser Gln Arg
        195                 200                 205

Leu Val Asp Ser His Gly Val Asp Val Val Ser Phe Thr Gly Ser Thr
210                 215                 220

Ala Thr Gly Lys Lys Ile Met Ala Ala Ala Asp Ser Met Lys Lys
225                 230                 235                 240

Leu Ser Leu Glu Leu Gly Gly Lys Ser Cys Cys Val Val Phe Asp Asp
                245                 250                 255

Ala Asp Val Ala Ala Ile Ala Pro Arg Leu Ala Arg Ala Ala Thr Ile
            260                 265                 270

Ile Ser Gly Gln Gln Cys Thr Ala Ala Arg Arg Val Leu Val His Ala
        275                 280                 285

Ser Arg Ala Ala Gln Met Arg Glu Gln Leu Ala Ser Ala Leu Ala Ser
290                 295                 300

Leu Arg Val Gly Pro Gly Ile Asp Pro Ala Thr Asp Ile Gly Ala Leu
305                 310                 315                 320

Ile Asp Gly Thr Thr Arg Asp Ala Val Ala Arg Thr Ile Glu Arg Ala
                325                 330                 335
```

```
Cys Gly Thr Ala Glu Arg Val Leu Leu Arg Gly Thr Cys Ser Gly His
            340                 345                 350

Ala Phe Leu Ser Pro Thr Leu Val Glu His Asp Asp Pro Lys Ala Phe
        355                 360                 365

Phe Cys Gln Asp Glu Ile Phe Gly Pro Phe Val Thr Leu Glu Val Phe
    370                 375                 380

Glu Asn Glu Met Glu Ala Ile Glu Lys Ala Asn Asp Thr Val Phe Gly
385                 390                 395                 400

Leu Ser Ala Ser Val Trp Thr His Asp Gly Ala Arg Ala Leu Arg Val
                405                 410                 415

Ala Arg Ala Leu Arg Asn Gly Thr Val Trp Ile Asn Asp His Asn Lys
            420                 425                 430

Leu Phe Ala Glu Ala Glu Thr Gly Gly Tyr Arg Gln Ser Gly Leu Gly
        435                 440                 445

Arg Leu His Gly Tyr Asp Ala Leu Ala Asp Phe Thr Glu Leu Lys His
    450                 455                 460

Ile Cys Met Pro Ala Gly Val Ala Glu Gly Ile Ala Pro Leu Arg
465                 470                 475

<210> SEQ ID NO 21
<211> LENGTH: 483
<212> TYPE: PRT
<213> ORGANISM: Burkholderia graminis C4D1M

<400> SEQUENCE: 21

Met Glu Arg Asp Ala Met Asn Trp Ile Ala Gly Glu Trp Ala Gly Lys
1               5                   10                  15

Pro Val Leu Ala Ser Ser Asp Pro Ser Asn Gly Glu Thr Leu Gly Arg
            20                  25                  30

Phe Val Ser Ser Asn Thr Gln Asp Ala Asp Ala Ala Val Ser Ala Ala
        35                  40                  45

Arg His Thr Phe Asp His Thr Thr Trp Ala Gln Asp Ala Arg Arg Arg
    50                  55                  60

Gln Asp Val Leu Leu Arg Trp Ala Gln Ala Leu Glu Leu Ser Val Glu
65                  70                  75                  80

Pro Leu Ala Glu Leu Leu Thr His Glu Asn Gly Lys Thr Ile Gly Gln
                85                  90                  95

Ala Arg Gly Glu Met Arg Ala Ala Ile Ser Glu Val Arg Tyr Tyr Ala
            100                 105                 110

Gly Leu Ala Arg His Ile Ala Gly His Val Ile Glu Pro Glu Pro Gly
        115                 120                 125

Thr Ile Ser Thr Met Leu Arg Glu Ala Ala Gly Val Ala Ala Ile Ile
    130                 135                 140

Val Pro Trp Asn Ala Pro Ala Val Leu Leu Val Arg Ser Leu Ala Pro
145                 150                 155                 160

Ala Leu Ala Ala Gly Cys Thr Ala Ile Val Lys Pro Ala Ala Gln Thr
                165                 170                 175

Ser Leu Ile Thr Ala Ala Met Ile Arg Cys Leu Asp Gln Pro Ala Leu
            180                 185                 190

Pro Ala Gly Ala Val Asn Leu Leu Leu Glu Asn Gly Ala Glu Ala Ala
        195                 200                 205

Ala Arg Leu Val Glu Ser Ala Asp Val Asp Val Ile Ser Phe Thr Gly
    210                 215                 220

Ser Thr Glu Val Gly Lys Arg Ile Met Arg Ala Ala Ala Asp Ser Met
```

```
            225                 230                 235                 240
Lys Arg Leu Ser Leu Glu Leu Gly Gly Lys Ser Cys Cys Leu Val Phe
                245                 250                 255

Glu Asp Ser Asp Val Lys Ala Ile Ala Pro Arg Leu Ala Arg Ala Ala
                260                 265                 270

Thr Ile Ile Ser Gly Gln Gln Cys Thr Ala Ala Arg Arg Ile Leu Val
                275                 280                 285

His Val Ser Lys Ala Asp Gln Met Arg Asp Glu Leu Val Lys Ala Leu
                290                 295                 300

Ala Ser Leu Lys Val Gly Pro Gly Ile Asp Pro Ala Ser Asp Ile Gly
305                 310                 315                 320

Ala Leu Ile Asp Ala Ala Ser Arg Asp Ala Val Gln Thr Thr Val Glu
                325                 330                 335

Arg Ala Cys Asp Leu Ala Asp Arg Val Leu Leu Arg Gly Thr Ser Ser
                340                 345                 350

Gly Pro Gly Ala Phe Leu Ser Pro Thr Leu Val Glu His Gly Glu Pro
                355                 360                 365

His Ala Phe Phe Cys Gln Asp Glu Ile Phe Gly Pro Phe Val Thr Leu
                370                 375                 380

Glu Thr Phe Val Thr Glu Lys Glu Ala Val Glu Lys Ala Asn Asn Thr
385                 390                 395                 400

Val Phe Gly Leu Ser Ala Ser Val Trp Thr His Asp Ser Ala Arg Ala
                405                 410                 415

Phe Arg Ile Ala Arg Ala Leu Arg Asp Gly Thr Val Trp Ile Asn Asp
                420                 425                 430

His Asn Arg Leu Phe Ala Glu Ala Glu Thr Gly Gly Tyr Arg Gln Ser
                435                 440                 445

Gly Leu Gly Arg Leu His Gly Tyr Asp Ala Leu Ala Asp Phe Thr Glu
                450                 455                 460

Ile Lys His Ile Cys Val Gly Ala Gly Val Leu Glu Gly Ile Glu Val
465                 470                 475                 480

Leu Gly Ser

<210> SEQ ID NO 22
<211> LENGTH: 483
<212> TYPE: PRT
<213> ORGANISM: Azospirillum sp. B510

<400> SEQUENCE: 22

Met Thr Asn Leu Asp Ser Arg His Trp Ile Asp Gly Ala Trp Val Pro
1               5                   10                  15

Gly Thr Asp Arg Phe Ala Ser Ile Asn Pro Ala Asp Gly Ser Val Leu
                20                  25                  30

Gly His Ala Ala Asp Gly Gly Arg Ala Glu Ala Glu Ala Ile Ala
                35                  40                  45

Ala Ala His Ala Ala Phe Asn Arg Pro Asp Trp Ala Gln Asn Pro Arg
                50                  55                  60

Leu Arg Gln Ser Ile Leu Leu Gly Trp Ala Asp Arg Leu Asp Thr Gln
65                  70                  75                  80

Ala Glu Asp Leu Ala Arg Leu Leu Thr Leu Glu Asn Gly Lys Ala Ile
                85                  90                  95

Ala Gln Ser Arg Gly Glu Ile Ala Gly Ala Ile Ser Glu Ile Arg Tyr
                100                 105                 110

Tyr Gly Gly Leu Ala Arg His Val Pro Gly His Val Leu Glu Val Glu
```

```
            115                 120                 125
Pro Gly Val Leu Ser Thr Met Leu Arg Glu Pro Ala Gly Val Ala Ala
        130                 135                 140

Leu Ile Ile Pro Trp Asn Ala Pro Val Leu Leu Ala Arg Ala Ile
145                 150                 155                 160

Gly Pro Ala Leu Ala Cys Gly Cys Thr Val Val Lys Pro Ala Ala
                165                 170                 175

Gln Thr Thr Leu Leu Thr Ala Ala Phe Leu Arg Ala Leu Ser Glu Val
            180                 185                 190

Pro Ser Leu Pro Arg Gly Val Cys Asn Met Ile Ser Glu Thr Gly His
        195                 200                 205

Ala Ala Ala Ala Arg Leu Val Asp Ser Pro Leu Val Asp Val Val Ser
210                 215                 220

Phe Thr Gly Ser Thr Ala Thr Gly Lys Arg Ile Met Val Ala Ala Ala
225                 230                 235                 240

Asp Thr Met Lys Lys Leu Ser Leu Glu Leu Gly Gly Lys Ser Cys Cys
                245                 250                 255

Leu Val Phe Pro Asp Ala Asp Pro Ala Glu Thr Ala Ala Arg Ile Ala
            260                 265                 270

Thr Ala Ala Thr Ile Ile Ser Gly Gln Gln Cys Thr Ala Ala Arg Arg
        275                 280                 285

Val Leu Val His Ala Ser Ala Phe Asp Ala Met Lys Thr His Leu Arg
        290                 295                 300

Ala Ala Leu Ala Ala Met Thr Val Gly Asn Gly Leu Asp Pro Ala Ile
305                 310                 315                 320

Arg Met Gly Pro Leu Ile Asp Arg Pro Ala Arg Asp Gln Val Gln Thr
                325                 330                 335

Gln Val Glu Arg Ala Phe Asp Ala Cys Asp Glu Val Leu Leu Arg Gly
            340                 345                 350

Gly Val Pro Thr Asp Ser Pro Ala Ala Ala Ser Phe Leu Thr Pro Ser
        355                 360                 365

Leu Val Ala His Asp Asp Pro Ser Ala Phe Phe Cys Gln Asp Glu Ile
        370                 375                 380

Phe Gly Pro Phe Val Val Leu Glu Arg Phe Glu Thr Glu Ala Glu Ala
385                 390                 395                 400

Val Ala Lys Ala Asn Asn Thr Val Phe Gly Leu Ser Ala Ser Val Trp
                405                 410                 415

Thr Arg Asp Gly Ala Arg Ala Leu Arg Met Ala Arg Ala Leu Arg Asn
            420                 425                 430

Gly Thr Val Trp Ile Asn Asp His Asn Arg Leu Phe Ala Glu Ala Glu
        435                 440                 445

Thr Gly Gly Tyr Arg Gln Ser Gly Leu Gly Arg Leu His Gly Tyr Asp
        450                 455                 460

Ala Phe Ala Asp Phe Thr Glu Leu Lys His Val Cys Gln Thr Val Gly
465                 470                 475                 480

Thr Ile Gly

<210> SEQ ID NO 23
<211> LENGTH: 480
<212> TYPE: PRT
<213> ORGANISM: Pseudomonas putida

<400> SEQUENCE: 23

Met Gln Ser Gln His Tyr Ile Asp Gly Gln Trp Thr Ser Thr Asp Arg
```

-continued

```
1               5                   10                  15
Trp Thr Asp Ser Leu Asp Pro Ala Ser Gly Glu Leu Ile Gly Cys Phe
                20                  25                  30
Ala Asp Gly Gly Glu Ala Glu Ala Ala Val Ala Ala Ala
            35                  40                  45
Arg Ala Phe Asn Asp Pro Gln Trp Ala Gln Asn Pro Arg Leu Arg Gln
        50                  55                  60
Gln Leu Leu Leu Glu Trp Ala Ala Gly Leu Lys Ala Arg Gln Glu Gln
65                  70                  75                  80
Leu Ala Gln Leu Leu Thr Arg Glu Asn Gly Lys Ala Leu Ala Gln Ser
                85                  90                  95
Arg Gly Glu Ile Gly Gly Ala Ile Ser Glu Ile Leu Tyr Tyr Ala Gly
                100                 105                 110
Leu Ala Arg His Asn Pro Gly His Met Leu Glu Val Ala Pro Gly Glu
                115                 120                 125
Phe Ser Ser Met Leu Arg Glu Pro Ala Gly Val Ala Gly Leu Ile Ile
        130                 135                 140
Pro Trp Asn Ala Pro Ala Val Leu Leu Val Arg Ala Leu Ala Pro Ala
145                 150                 155                 160
Ile Ala Ala Gly Cys Thr Val Val Ile Lys Pro Ala Pro Gln Thr Ala
                165                 170                 175
Leu Phe Asn Ala Ala Met Leu Glu Pro Leu Phe Ala Leu Pro Gly Leu
                180                 185                 190
Pro Ala Gly Ala Val Asn Leu Phe Ala Glu Ser Gly His Ala Gly Ala
        195                 200                 205
Ala His Leu Val Ala Ser Pro Arg Val Asp Val Leu Ser Phe Thr Gly
210                 215                 220
Ser Thr Ala Thr Gly Gln Arg Ile Met Arg Asp Cys Ala Ala Thr Met
225                 230                 235                 240
Lys Lys Leu Ser Leu Glu Leu Gly Gly Lys Ser Cys Cys Leu Val Phe
                245                 250                 255
Glu Asp Ala Asp Ile Ala Ala Ile Ala Pro Lys Leu Ala Ala Ala Ala
            260                 265                 270
Thr Ile Ile Ser Gly Gln Gln Cys Thr Ala Ala Arg Arg Val Leu Val
        275                 280                 285
His Ala Ser Arg Phe Ala Glu Met Lys Thr Ala Leu Ser Ala Ala Leu
        290                 295                 300
Gly Gln Ile Arg Leu Gly Asn Gly Leu Asp Pro Ala Asn Asn Met Gly
305                 310                 315                 320
Pro Leu Ile Asp Trp His Ser Arg Asp Ser Val Glu Arg Arg Ile Gly
                325                 330                 335
Glu Ala Leu Asp Ser Cys Asp Glu Val Leu Leu Ala Gly Gly Arg Pro
                340                 345                 350
Gln Gly Glu Leu Ser Lys Gly Ala Phe Leu Ala Pro Ser Leu Ile Ala
                355                 360                 365
His Arg Asp Ser Ser Ala Phe Phe Cys Gln Glu Glu Ile Phe Gly Pro
            370                 375                 380
Leu Leu Val Leu Glu Ser Phe Glu Asp Glu Thr Glu Ala Val Ala Arg
385                 390                 395                 400
Ala Asn His Thr Glu Phe Gly Leu Ser Ala Ser Val Trp Thr Asp Gln
                405                 410                 415
Gly Ala Arg Ala Trp Arg Val Ala Arg Ala Leu Arg Asn Gly Thr Val
            420                 425                 430
```

```
Trp Leu Asn Asp His Asn Arg Leu Phe Ala Glu Ala Glu Thr Gly Gly
            435                 440                 445

Tyr Arg Lys Ser Gly Leu Gly Arg Leu His Gly Val Asp Ala Leu Leu
    450                 455                 460

Asp Phe Ser Glu Leu Lys His Ile Tyr Gln Asn Val Gly Thr Leu Gly
465                 470                 475                 480

<210> SEQ ID NO 24
<211> LENGTH: 486
<212> TYPE: PRT
<213> ORGANISM: Rhodopseudomonas palustris BisB18

<400> SEQUENCE: 24

Met Gly Met Thr Ala Leu His Ala Asp Asn Leu Ile Asp Gly Ala Trp
1               5                   10                  15

Gln Pro Ala Gln Ser Gly Ala Thr Ala Pro Ser Leu Asp Pro Ser Ser
            20                  25                  30

Gly Gly Thr Ile Gly Gly Phe Ala Ala Gly Ala Ala Asp Ala Gln
        35                  40                  45

Ala Ala Val Ala Ala Ala Arg Arg Ala Phe Glu Arg Pro Glu Trp Ser
    50                  55                  60

Gln Asn Pro Arg Ala Arg Gln Met Val Met Leu Arg Trp Ala Asp Arg
65                  70                  75                  80

Met Glu Ala Gln Ala Asp Gln Leu Ala Arg Leu Leu Thr Leu Glu Asn
                85                  90                  95

Gly Lys Pro Leu Pro Gln Ser Arg Gly Glu Ile Ala Gly Ser Val Ser
            100                 105                 110

Glu Ile Arg Tyr Tyr Ala Gly Leu Thr Arg Tyr Ile Pro Gly His Val
        115                 120                 125

Phe Glu Val Glu Pro Gly Ser Phe Ser Thr Leu Leu Lys Glu Pro Ala
130                 135                 140

Gly Val Ala Gly Leu Ile Ile Pro Trp Asn Ala Pro Ala Val Leu Leu
145                 150                 155                 160

Ile Arg Ala Leu Thr Pro Ala Leu Ala Ala Gly Cys Thr Val Val Ile
                165                 170                 175

Lys Pro Ala Pro Gln Thr Ala Gln Ile Thr Ala Ala Ile Ile Lys Cys
            180                 185                 190

Leu His Glu Val Asp Gly Leu Pro Arg Gly Val Val Asn Leu Val Ser
        195                 200                 205

Glu Gln Gly His Gln Val Ala Glu His Leu Val Thr Ser Asn Asp Val
210                 215                 220

Asp Val Ile Ser Phe Thr Gly Ser Asn Ala Thr Gly Ala Arg Ile Met
225                 230                 235                 240

Ala Ala Ala Ala Pro Thr Met Lys Lys Leu Ser Leu Glu Leu Gly Gly
                245                 250                 255

Lys Ser Ala Cys Leu Val Phe Asp Asp Ala Asp Ile Ala Asp Val Ala
            260                 265                 270

Pro Lys Leu Ala Ala Ala Ala Thr Ile Ile Ala Gly Gln Gln Cys Thr
        275                 280                 285

Ala Ala Arg Arg Val Leu Val His Ala Ser Arg Tyr Asp Glu Met Lys
290                 295                 300

Ala Ala Leu Lys Ala Ala Leu Ala Asn Ile Arg Ile Ala Pro Gly Ser
305                 310                 315                 320

Ala Ala Gly Ala Glu Met Gly Pro Leu Ile Asp Ala Ala Ser Leu Ala
```

```
                        325                 330                 335
Ala Val Ala Lys Arg Ala Asp Glu Ala Met Gln Ala Ala Asp Glu Val
            340                 345                 350

Val Leu Arg Gly Gly Arg Pro Ala Gly Asp Leu Ala Asn Gly Tyr Phe
            355                 360                 365

Leu Ser Pro Thr Leu Val Ala His Arg Asp Thr Ser Ala Phe Phe Val
370                 375                 380

Gln Glu Glu Ile Phe Gly Pro Leu Val Val Leu Glu Lys Phe Glu Asp
385                 390                 395                 400

Glu Lys Glu Ala Val Ala Arg Ala Asn His Ser Asp Tyr Gly Leu Ser
                405                 410                 415

Ala Ser Val Trp Thr His Asp Gly Ala Arg Ala Met Arg Val Ala Arg
                420                 425                 430

Ala Leu Arg Asn Gly Thr Val Trp Ile Asn Asp His Asn Lys Leu Phe
            435                 440                 445

Ala Glu Ala Glu Thr Gly Gly Tyr Arg Arg Ser Gly Leu Gly Arg Leu
450                 455                 460

His Gly Tyr Asp Ala Leu Ile Asp Phe Leu Glu Ile Lys His Val Tyr
465                 470                 475                 480

Gln Ser Cys Gly Val Val
                485

<210> SEQ ID NO 25
<211> LENGTH: 485
<212> TYPE: PRT
<213> ORGANISM: Dinoroseobacter shibae DFL 12

<400> SEQUENCE: 25

Met Thr Thr Thr Asp Leu Ile Ala Arg His Met Ile Gly Gly Ser Tyr
1               5                   10                  15

Ser Asp Ala Gly Asp Lys Ile Ala Ser Ile Asn Pro Ala Thr Gly Ala
            20                  25                  30

Val Val Gly His Val Arg Ala Asp Gly Ala Ala Gln Ala Thr Ala Ala
        35                  40                  45

Ile Ala Ala Ala Arg Ala Ala Phe Asp Thr Thr Leu Trp Pro Gln Ser
    50                  55                  60

Pro Arg Asp Arg Gln Met Ala Leu Leu Arg Trp Ala Asp Ala Leu Glu
65                  70                  75                  80

Ala Asp Leu Ala Arg Leu Ala Glu Leu Leu Thr Leu Asn Gly Lys
                85                  90                  95

Pro Leu Gly Ala Ser Lys Gly Glu Leu Gly Ala Ala Ile Ser Glu Ile
            100                 105                 110

Arg Tyr Tyr Ala Gly Leu Thr Arg His Asn Pro Gly His Ala Met Glu
        115                 120                 125

Val Ala Pro Gly Glu Leu Ser Val Met Leu Arg Glu Pro Ala Gly Val
    130                 135                 140

Ala Gly Ile Ile Val Pro Trp Asn Ala Pro Ala Val Leu Leu Ile Arg
145                 150                 155                 160

Ser Leu Ala Pro Ala Leu Ala Val Gly Cys Thr Thr Val Thr Lys Pro
                165                 170                 175

Ala Pro Gln Thr Ala Leu Phe Thr Ala Ala Cys Met Ala Pro Leu Phe
            180                 185                 190

Glu Asp Ala Ala Ile Pro Ala Gly Val Val Asn Val Val Phe Glu Val
        195                 200                 205
```

```
Gly His Asp Ala Ala Gln Thr Leu Val Thr Ser Pro Asp Val Asp Val
    210                 215                 220
Ile Ser Phe Thr Gly Ser Asn Ala Val Gly Gln Arg Ile Met Ala Asp
225                 230                 235                 240
Ala Ala Pro Thr Met Lys Lys Leu Ser Leu Glu Leu Gly Gly Lys Ser
                245                 250                 255
Cys Cys Ile Val Leu Asp Asp Ala Asp Ile Gly Val Val Ala Pro Lys
                260                 265                 270
Leu Ala Ala Ala Thr Ile Ile Ser Gly Gln Gln Cys Thr Ala Ala
                275                 280                 285
Arg Arg Val Leu Val His Glu Ser Arg Leu Asp Glu Ala Lys Ser Ala
290                 295                 300
Leu Ser Ala Ala Leu Gln Ala Val Ser Ile Gly Asp Gly Met Ser Asp
305                 310                 315                 320
Gly Thr Ala Met Gly Pro Leu Ile Asp Ile Gln Ser Arg Asp Arg Val
                325                 330                 335
Met Arg Asp Cys Gly Thr Val Tyr Asp Thr Ala Asp Glu Val Val Leu
                340                 345                 350
Arg Gly Gly Pro Leu Asp Gly Pro Lys Gly Ser Ala Phe Met Ser Pro
        355                 360                 365
Ala Leu Val Val His Ser Asp Pro Asn Ala Ser Phe Val Gln Asp Glu
370                 375                 380
Ile Phe Gly Pro Leu Val Leu Glu Thr Phe Arg Asp Glu Ala Asp
385                 390                 395                 400
Ala Val Ala Lys Ala Asn Asn Thr Val Tyr Gly Leu Ser Ala Ser Ile
                405                 410                 415
Trp Thr His Arg Gly Asp Ala Ser Trp Arg Leu Ala Arg Ala Leu Arg
                420                 425                 430
Asn Gly Thr Val Trp Ile Asn Asp His Asn Arg Leu Phe Ala Glu Ala
            435                 440                 445
Glu Thr Gly Gly Tyr Arg Arg Ser Gly Leu Gly Arg Leu His Gly Phe
        450                 455                 460
Asp Gly Leu Leu Asp Phe Cys Glu Leu Lys His Val Tyr Gln Asn Val
465                 470                 475                 480
Gly Val Val Gly His
            485

<210> SEQ ID NO 26
<211> LENGTH: 1503
<212> TYPE: DNA
<213> ORGANISM: Cupriavidus basilensis HMF14

<400> SEQUENCE: 26
atgaacgcgc aacactggat tgccggcgcc tggaccggcg agccttccgc cgatagcgtc      60
aaccccgccg acgggaccct gatcgggcag ttcgcggacg gcggcacctg gcaagccgaa     120
gccgccatcg ccgccgcgcg ccatgtcttc gagcgcacca cctggggcca ggatgcccgc     180
ctgcgccagg acgtgcttct agcctgggct ggtgcgctcg aggcagagcg agagcgcctg     240
gccagcctgc tcaccgcgga aaacggcaag ccggtcgcac aagcccgagg cgaggtcggc     300
gccgcaattt cagaggtccg ctattacgcc gggctggcgc ggcacatccc gggtcacgtg     360
ctggagcccg agccaggcac gatatcgacc atcctgcgcg agccggccgg cgtcgccgcc     420
atcatcgtcc cctggaacgc gccggcggtg ctgctcgtgc gctccctcgc gccagcgctt     480
gccgcgggct gcacggcagt ggtcaaatcg gcagcgcaaa ccacgctgtt cacagccgca     540
```

```
atgctgcgct tgttcgagcg cacggccctg ccggccggcg ccgtcaatct ggtctgcgaa      600
acgggctatg cggcagcgga ccacctggtg cgttcgcgcg acgtggacgt agtgagcttc      660
acaggatcga ccgcaaccgg caagaagatc atgatcgccg ctgcggacag cgtgaaaaaa      720
ctctcgctgg aactcggcgg gaaatcgtgc tgcctggtgt cgacgacgt cgatgcgcaa       780 gcggtcgcga acggcttgc gcttgccgcc accgtcatct cgggccagca atgcaccgcc       840
gcgcggcgag tactggttca cgaagccatc gcgccacaga tgcgccggca cctgaccgag      900
gccctcgccg cgctgcgcct cgggcccggc atcgagcccg acacccaaat cggcccgctg      960
atcgaccacc cgacgcgcgc gatggtgagc gcgcaagtcg agcgcgcctg cgacgaggcg     1020
gacacggtcc tgctgcgcgg cacgatgccg ggcggcgcgc tagcgcgcgg cgccttcctc     1080
agccccacac tagtggaaca cagcgacccc ggtgccttct tctgccagga ggagatcttc     1140
gggcccttcg tcacattcga gaccttcgcg accgaagacg aggcgctagc caaggccaac     1200
aacaccgtct tcggcctgtc cgccagcgtc tggacgcacc acggcgagcg cgccatacgc     1260
ctagcgcggg cgctgcgcaa cggcacggtc tgggtcaacg accacaaccg cctgttcgcc     1320
gaagcggaga cgggcggcta tcggcaaagc ggccttggac ggctccacgg ttatgacgcc     1380
ctcgcggact tcaccgagtt gaagcacatc tgcatccagg cgggcctgcc gaaagggatg     1440
tcgcaggcgg gctgcaggct cagtggggta gcagcgcgcg agcggatggg agtttccgtc     1500
tag                                                                  1503

<210> SEQ ID NO 27
<211> LENGTH: 1440
<212> TYPE: DNA
<213> ORGANISM: Burkholderia sp. CCGE1002

<400> SEQUENCE: 27
atgaacgcac gacactggat tgccggcgaa tggaccggca cgcccaacat cgacagcatc       60
gatcccgcga cgggcgatgc catcggccgg ttcgccgacg gcggatcgag cgaagccgat      120
gccgccatcg ccgccgctcg ccacgcgttc gatcgcacga catgggcgca ggacgcgcgc      180
ttgcgccagg acgtgctact cggctgggct tcggcgctcg aagccgaacg cgacatgctc      240
gcgacgctgc tcacgcgtga aaacggcaag gcgatcgcgc aatcgcgcga cgagattgcc      300
ggcgcgatat cggaggtgcg ctattacgcg gggctcgcgc gccatattgc cgggcacgtg      360
ctcgaaccgg aaccgggcac gatatcgacg atgctgcgcg aagcggccgg cgtcgcggcg      420
atcatcgtgc cgtggaatgc gcccgccgtg ctgctcgtgc gctcgctcgc gcccgctctc      480
gcggccggct gcacggtgat agtcaaaccg gcggcgcaaa cgtcgctgct cacggccgcg      540
atgttgcgct gcttcgaaca cacggcgttg cctgaaggcg cggtgaacct agtcaacgaa      600
cggggatacg cggccagcca gcggctcgtc gactcgcacg gggtcgacgt ggtgagcttc      660
acgggatcga cggcgacggg caagaagatc atggcggccg ctgccgacag catgaagaag      720
ctgtcgctcg aacttggcgg caagtcatgc tgcgtcgtct tcgacgatgc cgatgtcgcg      780
gcgatcgcgc gcgtctcgc gcgcgccgcg acgatcatct ccgggcagca atgcacggcg      840
gcgcgccggg tgctggttca tgcgtcgcgc gctgcgcaaa tgcgcagcca gctcgcgtcg      900
gcgcttgcgt cgctgcgggt cggaccgggc atcgatccgg cgacggatat cggcgcgctc      960
atcgacggca ccacgcgcga tgcggtggca cggacgatcg agcgcgcgtg cggaacggcc     1020
gagcgtgtgc tgctgcgagg cacttgctcg gggcacgcgt ttctgtcgcc gacgctcgtc     1080
```
gagcatgacg atccgaaggc gttcttttgc caggacgaga tctttggccc gttcgtcacg 1140
ctggaagtct tcgagaacga aatggaagcg atcgagaaag ccaacgacac ggtcttcggt 1200
ctctcggcga gcgtatggac gcacgacgga gcgcgcgcat tgcgcgtcgc gcgtgcgctg 1260
cgcaacggca cggtgtggat caacgaccac aacaagcttt tcgccgaagc cgaaacgggc 1320
gggtatcgcc aaagcggact gggtcggctg cacggctacg atgcgctggc ggacttcacc 1380
gagttgaagc acatctgcat gccggccggc gtggcggaag gtatcgcgcc gttgcggtga 1440

<210> SEQ ID NO 28
<211> LENGTH: 1452
<212> TYPE: DNA
<213> ORGANISM: Burkholderia graminis C4D1M

<400> SEQUENCE: 28
atggaaagag acgctatgaa ttggatcgcc ggcgaatggg ccggcaagcc cgtgctcgca 60
agctccgatc cttcgaacgg agagacgctc ggccggttcg tcagctcgaa cacgcaagac 120
gcggacgccg ccgtctcggc tgcccgccat acgttcgatc acacaacgtg ggcacaggat 180
gcccgtcgac ggcaggatgt tctgcttcgc tgggcgcaag ctctcgagtt gtcggtggaa 240
ccgctagcgg aattgctgac gcatgaaaac ggcaagacta ttgggcaggc gcgaggagaa 300
atgcgcgccg caatttccga agtgcgctac tacgcgggac tcgcgcgcca cattgccggt 360
cacgtcatcg agcccgagcc aggcaccatc tcgacgatgt tgcgcgaggc cgccggcgtt 420
gctgcgatca tcgtgccgtg gaacgctccc gccgtgctgc tcgtgcggtc ccttgcgccc 480
gccctcgctg ccggatgcac ggccatcgtc aagccggctg cccagacgtc attgatcacc 540
gcggcaatga tccgttgtct cgaccagccg gcgcttcccg ccggtgctgt caatctgctt 600
ctcgaaaacg gcgcagaagc cgctgcgcga ctggtcgagt ccgccgatgt cgatgtgatc 660
agctttacgg gttcgacgga agtcggcaag cgaatcatgc gcgccgctgc agacagcatg 720
aagcgattgt cgcttgagct gggcggcaaa tcgtgttgtc tcgtcttcga ggacagcgac 780
gttaaggcca ttgcacctcg tcttgcccgg gccgcgacca tcatctccgg acaacaatgc 840
accgctgcac ggcgaatact cgtgcatgtg tcaaaggcgg accaaatgcg agacgaactc 900
gtcaaagcac tcgcaagcct caaggttggc ccagggatcg atcccgcttc cgacattggc 960
gcgctgatcg atgctgcgtc ccgcgacgct gtccagacca cggttgaacg agcgtgtgac 1020
cttgcagatc gcgtgctctt gcgcgggact tcgagcggac cgggcgcctt tctgtcaccg 1080
acgctggtcg agcacggaga acctcacgcc ttcttttgcc aggacgagat ctttggcccg 1140
ttcgtcacgt tagagacctt tgtgaccgaa aaggaagccg ttgaaaaggc aaacaacacc 1200
gtttttggcc tgtccgcgag cgtgtggacc cacgactcgg ctcgggcttt ccggattgcg 1260
cgtgcgctgc gtgatgggac cgtctggatc aacgaccaca acaggttgtt cgcagaggcc 1320
gaaactggcg gctatcggca gagcggactg ggccggttgc acggctatga cgcgctagcg 1380
gacttcacgg agatcaagca tatctgtgtc ggtgcaggag tcctggaagg catcgaagtg 1440
cttggctcgt ga 1452

<210> SEQ ID NO 29
<211> LENGTH: 1452
<212> TYPE: DNA
<213> ORGANISM: Azospirillum sp. B510

<400> SEQUENCE: 29
gtgaccaact tggacagccg gcattggatc gacggcgcat gggtgcccgg caccgaccgc 60

```
ttcgccagca tcaaccccgc cgacggcagc gtcctcggcc atgccgccga tggcggacgc    120
gccgaggccg aggccgccat cgccgccgcg catgccgcct tcaatcggcc cgactgggcg    180
caaaacccgc ggctgcgcca atccatcctg ctcggctggg ccgacaggct cgacacgcaa    240
gccgaggatc tcgcccgcct gctgacgctg gagaacggca aggccatcgc ccagtcgcgg    300
ggcgagatcg ccggcgccat ttcggaaatc cgctattacg gcggcctcgc tcgccatgtt    360
cccggccatg tgctggaggt cgagccgggc gtgctgtcca ccatgctgcg agagccggcc    420
ggcgtggcgg cgctgatcat tccgtggaat gcgccggcgg tgctgctggc gcgggccatc    480
ggtccggcgc tggcctgcgg ctgcaccgtc gtggtcaagc cggcggcaca gaccaccttg    540
ctgaccgccg ccttcctgcg cgccctgtcc gaggttccca gcctgccccg cggcgtctgc    600
aacatgatca gcgagaccgg ccatgccgcc gccgcccgcc tggtcgactc gccgttggtc    660
gacgtggtca gcttcaccgg ctccaccgcc accggcaagc gcatcatggt cgcggcggcg    720
gacaccatga agaagctgtc gctggagctg gcggcaaga gctgctgctt ggtcttcccc    780
gacgccgatc cggcagagac cgcggcgcgc atcgccaccg ccgccaccat catctccggc    840
cagcaatgca ccgccgcccg ccgggtgctg gtccatgcat cggccttcga cgcgatgaag    900
acacatctgc gggcagcgtt ggcggccatg acggtgggga acggcctcga tccggcgata    960
cggatgggac cgctgatcga ccggccggcg cgcgatcagg tgcagaccca ggtcgaacgg    1020
gccttcgatg cctgcgacga ggtgctgctg cgtggcgggg tgccgacgga cagccccgcc    1080
gccgcgtcgt tcctcacccc atcgctggtg gcgcacgacg accctccgc cttcttctgc    1140 caggacgaga ttttcggccc cttcgtcgtg ctggagcgct tcgagaccga agcggaggcg    1200
gtggccaagg ccaacaacac cgtgttcggc ctgtcggcca cgtctggac ccgcgacggc    1260 gcccgggcgt tgcgcatggc ccgggcgttg cgcaatggaa ccgtctggat caacgaccac    1320
aaccgcctgt tcgccgaggc ggaaacaggg ggctaccggc aaagcggcct gggccggttg    1380
cacggctacg atgccttcgc cgatttcacg gaactgaagc atgtttgcca gacggtggga    1440
accattggct ga                                                       1452
```

<210> SEQ ID NO 30
<211> LENGTH: 1443
<212> TYPE: DNA
<213> ORGANISM: Pseudomonas putida

<400> SEQUENCE: 30

```
atgcaaagcc aacactacat cgatggacaa tggacctcaa cggatcgttg gaccgacagt     60
ctcgacccgg caagcggcga actgatcgga tgctttgccg acggcggcga ggccgaagct    120 gaagcggcg tggcagcggc cgcccgagcc ttcaacgacc gcaatgggc gcagaatcca    180 cgcctgcgtc agcagctatt gctggagtgg gctgccggcc tgaaggcgcg tcaggaacaa    240
ctcgcgcaat tgctgacgcg cgagaacggc aaggcattgg cgcagtcccg aggagagatc    300 ggcgggcta tttccgagat tcttttactac gccggcctgg ccggcataa cccggggcac    360 atgctagaag tggcgcccgg tgagttctcc agcatgctgc gcgaaccgc cggggtggcg    420 gggctgatca ttccatggaa tgccccgcg gtgctgctgt tcgtgctct ggcgccagcg    480 atcgcggcgg gttgtacagt ggtgatcaaa cccgcgccgc aaaccgcgct attcaatgct    540
gcgatgctcg aaccgctgtt cgcattgcca ggctgccgg ctgggggcggt caatctattc    600 gccgagagcg ggcatgccgg ggctgcgcat ttggtggctt cgccacgggt ggacgtgctc    660
```

```
agcttcaccg gctcgactgc tacgggccag cgcatcatgc gcgactgcgc ggcgactatg   720
aagaagctct ctctggaact gggcgggaaa tcttgctgcc tggtcttgga agatgccgat   780
attgccgcca tcgcgccgaa actggcagcg gcggccacca ttatctctgg ccagcaatgc   840
actgccgccc ggcgcgtact ggtgcatgcc agccgtttcg ccgaaatgaa aaccgcgctg   900
agcgccgcac tggggcagat ccgcctgggt aatggcctcg atccagcgaa caacatggga   960
ccgctgatcg actggcattc ccgggacagc gttgagcggc gcattggcga ggcgctggac  1020
agctgtgacg aagtgctgct ggccggaggt cgcccgcagg gtgaactgag caaaggcgca  1080
tttctcgcgc cgtcgctgat cgcccatcgc gacagcagcg cattcttttg tcaggaagaa  1140 attttggcc cgttgctggt actggagtcg ttcgaagacg aaaccgaggc tgtagcgcgc  1200
gccaaccata ccgagttcgg tctgtccgcg agtgtctgga ccgatcaggg tgctcgcgcc  1260
tggcgtgtcg ctcgggcact gcgcaacggt acggtgtggc tcaacgacca caacagattg  1320
tttgccgagg cggaaaccgg tggctatcga aagagcggtc tggggcgctt gcatggcgtc  1380
gatgcgctgc tggatttcag cgagctcaaa cacatttatc agaacgtcgg cacgctcggt  1440
tga                                                                1443

<210> SEQ ID NO 31
<211> LENGTH: 1461
<212> TYPE: DNA
<213> ORGANISM: Rhodopseudomonas palustris BisB18

<400> SEQUENCE: 31
atgggcatga ctgctctgca tgcggataat ctgatcgacg gcgcctggca gccggcgcaa    60
tccggcgcca cggcgccgag ccttgatccg tcgagcggcg cacgatcgg tggcttcgcg    120 gctggtggcg cggcggatgc gcaggccgcg gtagcggcgg cgcggcgcgc cttcgagcgg   180
ccggagtggt cgcagaaccc gcgggcgcgg cagatggtga tgctgcgctg gccgaccgg   240 atggaggcgc aggccgatca gctcgcccgg ctgctgacac tggagaacgg caagccgctg   300
ccgcagtcgc gcggcgaaat cgccggcagc gtctcggaga tccgttatta cgccgggctc   360
acgcgttaca tccccggcca cgtgttcgag gtcgagccgg cagtttctc gacgttgttg    420 aaagaaccgg ccggcgtcgc cggactgatc attccgtgga acgcgccggc ggtgctgctg   480
atccgcgcgc tgacgccggc gctcgccgcc ggctgcaccg tggtgatcaa gccggcgccg   540
cagaccgcgc agatcaccgc cgcgatcatc aaatgcctgc acgaggtcga cgggctgccg   600
cgcggcgtgt caatctggt cagcgagcag ggccaccaag tggccgagca tctggtgacc   660
tcgaacgacg tcgacgtcat cagcttcacc ggctccaacg ccaccggcgc gcggatcatg   720
gcggcggcgc gccgaccat gaagaaactg tcgctcgagc tcggcggcaa atccgcttgc   780
ctggtgttcg acgacgccga tatcgccgac gtggctccga agctcgccgc tgccgccacc   840
atcatcgccg ccagcaatg caccgccgcg cgccgcgtgc tggtgcatgc ctcgcgctac   900
gacgagatga aggcggcgct gaaagccgcg ctggcgaaca tccgcattgc gccgggcagc   960
gcggcgggcg ccgagatggg tccgctgatc gacgcagcct cgctggccgc cgtggcgaag  1020
cgcgccgacg aggcgatgca ggccgccgac gaggtggtgc tgcgcggcgg caggcccgcc  1080
ggcgacctcg ccaacggtta cttcctgtcg ccgacgctcg tggcgcatcg cgacacgtcg  1140
gcgttcttcg tccaggaaga gatttttggg ccgctggtgg tgctcgaaaa attcgaggac  1200
gagaaggagg cggtggcccg cgccaatcac agcgactacg gctgtccgc cagcgtgtgg  1260 acccatgacg gcgcccgcgc gatgcgggtg gcgagggcgc tgcgcaacgg cacggtgtgg  1320
```

```
atcaacgacc acaacaagct attcgccgaa gccgagaccg gcggttatcg ccgcagcggg    1380
ctcggccgcc tgcacggcta tgacgcgctg atcgacttcc tcgagatcaa gcacgtctat    1440
cagagctgcg gcgtagtgta g                                              1461

<210> SEQ ID NO 32
<211> LENGTH: 1458
<212> TYPE: DNA
<213> ORGANISM: Dinoroseobacter shibae DFL 12

<400> SEQUENCE: 32
atgacaacga cggacctgat cgcgcggcac atgatcggcg gctcctattc ggacgcgggc      60
gacaagatcg cgtcgatcaa cccggcgacc ggggcggtcg ttgggcatgt ccgggccgac     120
ggcgcggcgc aggccacagc cgccattgcc gccgcgcggg ccgcattcga cacaacgctc     180
tggccgcaat caccccgcga ccggcagatg gccctgctgc ggtgggccga cgcgctggag     240
gccgatctcg cacggcttgc ggaattgctg acgttgacca atggcaaacc gcttggcgcg     300
tccaagggcg aattgggcgc ggcgatatcg gaaatccgat actatgcggg cctgacccgc     360
cacaatcccg ccacgcgat ggaagtggcg ccgggcgagc tttcggtgat gctgcgcgag     420
```
(partial — due to length limits)

```
<211> LENGTH: 28
<212> TYPE: DNA
<213> ORGANISM: Artificial Sequence
<220> FEATURE:
<223> OTHER INFORMATION: Synthetic

<400> SEQUENCE: 34
atgcggccgc gcgtcggggt cggtgcta                                           28
```